United States Patent
Movileanu et al.

(10) Patent No.: US 8,916,684 B2
(45) Date of Patent: Dec. 23, 2014

(54) BIOENGINEERED PROTEIN PORES

(75) Inventors: Liviu Movileanu, Jamesville, NY (US); Mohammad M. Mohammad, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 257 days.

(21) Appl. No.: 13/173,337

(22) Filed: Jun. 30, 2011

(65) Prior Publication Data
US 2012/0003694 A1 Jan. 5, 2012

Related U.S. Application Data

(60) Provisional application No. 61/359,952, filed on Jun. 30, 2010.

(51) Int. Cl.
*C12P 21/06* (2006.01)
*C12N 15/74* (2006.01)
*C07K 1/00* (2006.01)
*C07K 14/245* (2006.01)

(52) U.S. Cl.
CPC .................................. *C07K 14/245* (2013.01)
USPC ........................... 530/350; 435/471; 435/69.1

(58) Field of Classification Search
None
See application file for complete search history.

(56) References Cited

U.S. PATENT DOCUMENTS

2006/0051362 A1   3/2006   Jacques et al.

FOREIGN PATENT DOCUMENTS

RU      2333955       9/2008
WO   2007119891    10/2007

OTHER PUBLICATIONS

Nallani et al., A nanocompartment system (Synthosome) designed for biotechnological applications; Journal of Biotechnology, vol. 123, pp. 50-59, 2006.*
Endriss et al., Loop Deletions Indicate Regions Important for FhuA Transport and Receptor Functions in *Escherichia coli*; J Bact, vol. 186, No. 14, pp. 4818-4823, 2004.*
Thompson et al., Transproteomic Evidence of a Loop-Deletion Mechanism for Enhancing Protein Thermostability; JMB, vol. 290, pp. 595-604, 1999.*
Lahti et al., Interrogating and Predicting Tolerated Sequence Diversity in Protein Folds: Application to E. elaterium Trypsin Inhibitor-II Cystine-Knot Miniprotein; PLoS Computational Biology, vol. 5 No. 9, pp. 1-9, 2009.*
Noor Muhammad, et al, Engineering of the *E. coli* Outer Membrane Protein FhuA to overcome the Hydrophobic Mismatch in Thick Polymeric Membranes', Journal of Nanobiotechnology, vol. 9(8), pp. 1-9 (Mar. 17, 2011, online publication http://www.jnanobiotechnology.com/content/9/1/8). See Abstract, Whole document.
V. Braun, et al., 'Inactivation of FhuA at the Cell Surface of *Escherichia coli* K-12 by a Phage T5 Lipoprotein at the Periplasmic Face of the Outer Membrane, Journal of Bacteriology, vol. 176(15), pp. 4710-4717 (Aug. 1994), See Abstract, Tabel 2, Fig. 1.

* cited by examiner

*Primary Examiner* — Jennifer Dunston
*Assistant Examiner* — Addison D Ault
(74) *Attorney, Agent, or Firm* — David L. Nocilly; Bond Schoeneck & King, PLLC

(57) ABSTRACT

A mutant *Escherichia coli* β-barrel monomeric protein pore bioengineered to remove a lumen-occluding domain and modify some of its extracellular domains. The modified protein, FhuA Δ/CΔ4L, forms a highly conductive pore as compared to other known pores and is capable of sensing large polypeptides and discriminating between modified protein analytes.

7 Claims, 25 Drawing Sheets

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gtgatcgaag ctgtagccga c                                              21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
aatgcttaca gcaaacagtg t                                              21

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
gcgcaggttc tgacgcacag t                                              21

<210> SEQ ID NO 4
<211> LENGTH: 42
<212> TYPE: DNA
<213> ORGANISM: Artificial Sequence
```

```
<220> FEATURE:
<223> OTHER INFORMATION: Primer

<400> SEQUENCE: 4
actaccgcgt ggcagcagaa acgaaaggt tgcggtggca ac                        42

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5
catcatcacc atcaccacta aagcgctggg agccccccca gt                       42

<210> SEQ ID NO 6
<211> LENGTH: 31
<212> TYPE: PRT
<213> ORGANISM: Escherichia coli

<400> SEQUENCE: 6

Tyr Tyr Gly Trp Leu Pro Lys Glu Gly Thr Val Glu Pro Leu Pro Asn
1               5                   10                  15

Gly Lys Arg Leu Pro Thr Asp Phe Asn Glu Gly Ala Lys Asn Asn
            20                  25                  30

<210> SEQ ID NO 7
<211> LENGTH: 22
<212> TYPE: PRT
<213> ORGANISM: Escherichia coli

<400> SEQUENCE: 7

Cys Ser Asp Pro Ala Asn Ala Tyr Ser Lys Gln Cys Ala Ala Leu Ala
1               5                   10                  15

Pro Ala Asp Lys Gly His
            20

<210> SEQ ID NO 8
<211> LENGTH: 31
<212> TYPE: PRT
<213> ORGANISM: Escherichia coli

<400> SEQUENCE: 8

Asp Asp Ser Val Pro Leu Leu Asn Leu Tyr Asn Pro Pro Asp Asp Leu
1               5                   10                  15

Ala Val Asn Thr Asp Phe Asp Phe Asn Ala Lys Asp Pro Ala Asn
            20                  25                  30

<210> SEQ ID NO 9
<211> LENGTH: 23
<212> TYPE: PRT
<213> ORGANISM: Escherichia coli

<400> SEQUENCE: 9

Asn Leu Phe Asp Arg Glu Tyr Val Ala Ser Cys Phe Asn Thr Tyr Gly
1               5                   10                  15

Cys Phe Trp Gly Ala Glu Arg
            20

<210> SEQ ID NO 10
<211> LENGTH: 5
<212> TYPE: PRT
```

```
<213> ORGANISM: Artificial Sequence
<220> FEATURE:
<223> OTHER INFORMATION: short peptide replacement for loop domain

<400> SEQUENCE: 10

Asn Ser Glu Gly Ser
1               5
```

BIOENGINEERED PROTEIN PORES

CROSS-REFERENCE TO RELATED APPLICATIONS

The present application claims the priority of U.S. Provisional Application No. 61/359,952 entitled "Bioengineered Protein Pores" filed on Jun. 30, 2010, the entire contents of which are incorporated herein by reference.

BACKGROUND OF THE INVENTION

1. Field of the Invention

The present invention relates to modified protein pores, and, more specifically, to bioengineered protein pores that can be utilized as biosensors.

2. Description of the Related Art

Protein-based nanosensors represent an emergent alternative to current analytical devices in biomedical molecular diagnosis, because of the enhanced selectivity, specificity, and versatility of the protein receptor-ligand recognition. In the last decade, significant progress in protein engineering has enabled the design, synthesis, and purification of protein nanopores customized to execute numerous complex tasks. Currently, the engineering of biological nanopores is focused on pore-forming toxins and bacterial outer membrane proteins, because their robust β-barrel structure makes them the convenient choice for developing sensing technologies. The major benefits of using protein nanopores include knowledge of their accurate structure at atomic resolution, the ability to implement functional groups at strategic positions within their interior, and great prospects for parallelization and integration into nanofluidic devices. Despite these advantageous features, one persistent limitation is the lack of a methodology for preparing stiff protein scaffolds that maintain their functionality under a wide spectrum of environmental conditions. Moreover, these protein nanopores are multimeric, a trait that causes their targeted design to be a tedious and laborious process, because of the numerous permutations and combinations of engineered and native subunits within the same heteromeric protein.

The protein which has served as a benchmark and the archetype for the engineering of proteins nanopores is the staphylococcal endotoxin α-hemolysin ("αHL"). While this protein has been the mainstay of nanopore engineering, it does have two major limitations. First, it has a narrow constriction point with a diameter of 1.5 nm, therefore limiting this pore to the detection of small chemicals and analytes which are less than 1.5 nm in diameter. Second, the heptameric nature of this protein makes the engineering of the protein difficult. Recently, the former limitation has been overcome by engineering the 3.6 nm-wide phi29 motor protein to serve as channel forming nanopore (2.6 hemolysin diameters ("HD")), which permits the translocation of dsDNA (~2 nm). Yet, this newly engineered pore is dodecameric, and, similar to the αHL pore, its stoichiometry still poses a limitation to engineering. Thus, a monomeric β-barrel wider protein pore is still highly desired for protein engineering for future biosensing applications that involve proteins analytes and dsDNA.

BRIEF SUMMARY OF THE INVENTION

It is therefore a principal object and advantage of the present invention to provide a bioengineered protein pore.

It is a further object and advantage of the present invention to provide a bioengineered protein pore that can be utilized as a biosensor.

It is yet another object and advantage of the present invention to provide a bioengineered protein pore with a wide pore.

It is another object and advantage of the present invention to provide a monomeric protein pore that can be engineered to serve as a biosensor.

It is a further object and advantage of the present invention to provide a bioengineered, monomeric, β-barrel wider protein pore.

Other objects and advantages of the present invention will in part be obvious, and in part appear hereinafter.

In accordance with the foregoing objects and advantages, the present invention provides an engineered outer membrane protein that can be used as a biosensor. According to one embodiment of the present invention, the protein is a bacterial outer-membrane protein such as ferric hydroxamate uptake component A ("FhuA") from *Escherichia coli*. FhuA is a monomeric, 22-stranded β-barrel protein with a luminal cross-sectional side of 3.6×4.1 nm and thus offers a unique opportunity to engineer a pore with the dimensions suitable enough to serve as a stochastic sensor for large biomolecules and biomolecular complexes. According to one embodiment of the present invention, FhuA was engineered to remove its lumen-occluding cork domain (residues 1-160) and modify its extracellular loops which resulted in a ~33% reduction in the number of amino acids. The resultant channel-forming protein possessed a measured conductance of ~3.9 nS.

According to a second aspect of the present invention, a method for designing and engineering proteins such as β-barrel pores to serve as biosensors with a wide and/or specific pore is provided.

According to a third aspect of the present invention is provided an isolated nucleic acid encoding an engineered ferric hydroxamate uptake component A ("FhuA") protein, wherein said engineered FhuA protein is missing the cork domain and at least four of the eleven loop domains found in the wild-type FhuA protein. In a preferred embodiment, the missing cork domain comprises the first 160 amino acid residues of the wild-type FhuA protein. The missing loop domains can be replaced by a short amino acid sequence, including the sequence NSEGS (SEQ. ID NO: 10), among others. The missing loop domains can be, for example, loops 3, 4, 5, and 11, among other combinations, where loop 3 comprises amino acid residues 243 through 273 of the wild-type FhuA protein, loop 4 comprises amino acid residues 318 through 339 of the wild-type FhuA protein, loop 5 comprises amino acid residues 394 through 419 of the wild-type FhuA protein, and loop 11 comprises amino acid residues 682 through 704 of the wild-type FhuA protein. The sequence can be derived from an *E. coli* nucleic acid encoding a FhuA protein, among other sources.

According to a fourth aspect of the present invention is provided a method for obtaining an engineered ferric hydroxamate uptake component A ("FhuA") protein comprising the step of expressing a modified gene sequence in a host cell whereby a engineered FhuA protein is produced, where the modified gene sequence encodes an engineered FhuA protein that is missing the cork domain and at least four of the eleven loop domains found in the wild-type FhuA protein. In one embodiment, the method further comprises the steps of: (i) purifying the produced engineered FhuA protein; (ii) using the engineered FhuA protein as a sensor; and/or (iii) using the engineered FhuA protein as a transport protein According to a fifth aspect of the present invention is provided an isolated polypeptide encoding an engineered ferric hydroxamate uptake component A ("FhuA"), where the engineered FhuA missing the cork domain and at least four of the eleven loop domains found in the wild-type FhuA protein.

According to a sixth aspect of the present invention is provided a biosensor comprising an isolated polypeptide encoding an engineered ferric hydroxamate uptake component A ("FhuA"), where the engineered FhuA is missing the cork domain and at least four of the eleven loop domains found in the wild-type FhuA protein.

BRIEF DESCRIPTION OF THE SEVERAL VIEWS OF THE DRAWINGS

The present invention will be more fully understood and appreciated by reading the following Detailed Description in conjunction with the accompanying drawings, in which.

DETAILED DESCRIPTION OF THE INVENTION

The use of protein nanopores in medical biotechnology is constrained with two major challenges. First, the majority of the protein nanopores are small in diameter and thus do not allow for the sensing of large biomolecules. Second, they are multimeric in nature which creates a multitude of challenges in their engineering and functionalization.

Figure 1:
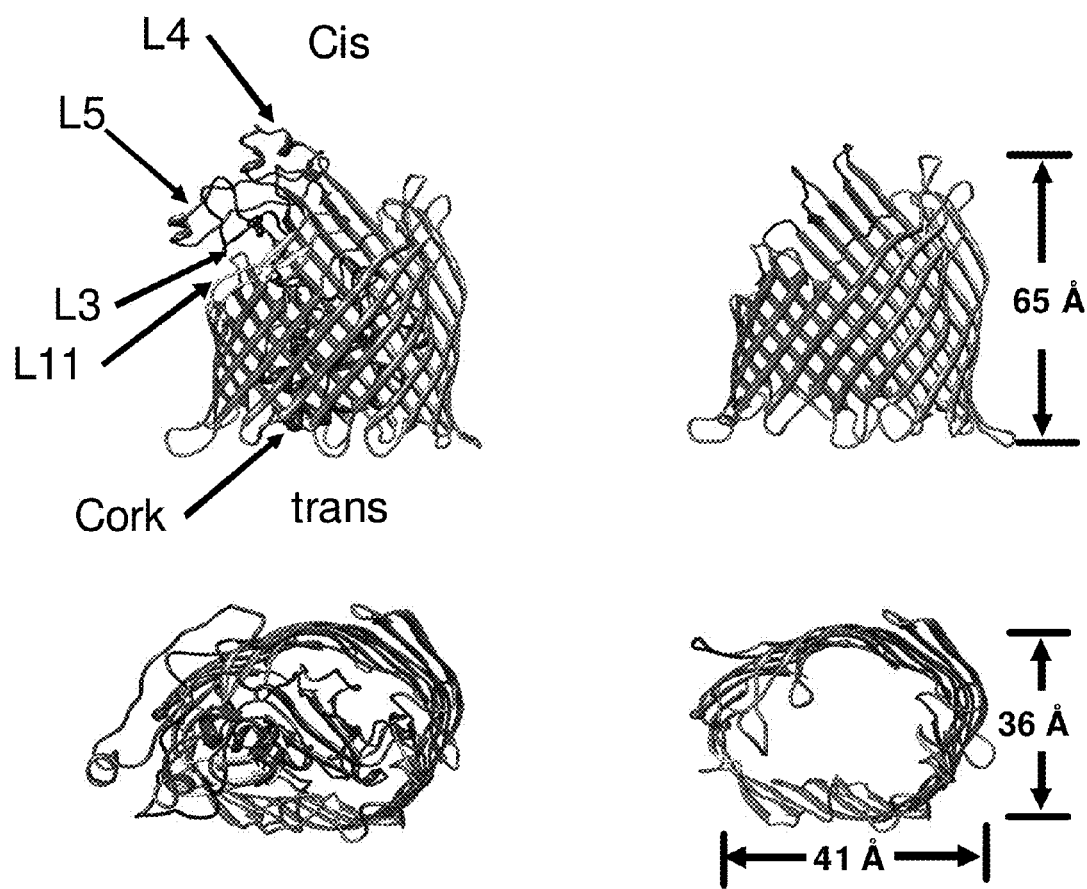
FIG. 1 is a ribbon diagram of wild-type FhuA ("WT-FhuA") (left) and engineered FhuA ΔC/Δ4L (right) proteins, with a side view (top) and an extracellular view (bottom)

To overcome these challenges, the *E. coli* outer-membrane protein FhuA was chosen for the design of a biosensor of desired specifications. Structurally, FhuA is a 714-residue β-barrel protein composed of 22 antiparallel β strands (residues 161-714), as revealed by high resolution x-ray crystal structure and as depicted in FIG. 1. The β-barrel of the native FhuA protein contains a globular N-terminal domain (residues 1-160) called the cork. The β-barrel domain has an elliptically shaped cross-sectional area, and the sequential β strands run anti-parallel to one another, conferring an exceptional robustness. The β strands are linked by eleven long loops on the extracellular side and eleven short turns on the periplasmic side. Further information about each of the loops is provided in TABLE 1. The x-ray crystal structure of the FhuA protein indicates that, unlike porins, the extracellular loops do not fold back into the interior of the pore but rather project away from the membrane surface. A distinctive feature of this outer membrane protein is its remarkable variety of functionalities, including the dual task of transporter and receptor.

TABLE 1

Physical properties of the extracellular loops of the FhuA protein

| Loop | Overall Charge | Charge Ratio | Residues | Loop Length (Å) | Comments |
|---|---|---|---|---|---|
| L1 | −1 | 0/−1 | Thr$^{170}$-Ser$^{172}$ | 7.0 | Very short loop |
| L2 | +1 | +1/0 | Ala$^{203}$-Ser$^{208}$ | 17.5 | Short loop |
| L3 | 0 | +4/−4 | Tyr$^{243}$-Asn$^{273}$ | 105 | Large flexible, random coil loop that folds back into the pore lumen |
| L4 | +1 | +3/−2 | Cys$^{318}$-His$^{339}$ | 73.5 | Large loop that contains three helices, and a β strand. The loop also contains a stabilizing disulfide bridge Cys$^{318}$-Cys$^{329}$; L4 along with part of the β strands block the access to the pore lumen |
| L5 | −4 | +3/−7 | Asp$^{394}$-Asn$^{419}$ | 87.5 | Large loop that contains a β strand, which partially occludes the pore lumen |
| L6 | +1 | +1/0 | Arg$^{463}$-Gly$^{466}$ | 10.5 | Very short loop |
| L7 | 0 | +1/−1 | Pro$^{502}$-Pro$^{515}$ | 45.5 | Flexible loop that does not appear to enter or block the pore lumen |
| L8 | −2 | 0/−2 | Asp$^{552}$-Phe$^{559}$ | 24.5 | Short loop |
| L9 | +1 | +2/−1 | Asp$^{598}$-Lys$^{611}$ | 45.5 | Medium sized flexible loop; the movement of L9 does appear to be restricted due to its positioning between two uneven β strands |
| L10 | 0 | +1/−1 | Gly$^{640}$-Ser$^{654}$ | 49.0 | Medium sized flexible loop that has potential to block the pore lumen |
| L11 | −2 | +1/−3 | Asn$^{682}$-Arg$^{704}$ | 77.0 | Large loop that contains an anti-parallel β sheet, which protrudes into the pore lumen |

In vivo, the FhuA protein exhibits a highly diverse functionality. Its primary role is to facilitate the energy-driven, high-affinity $Fe^{3+}$ uptake complexed by the siderophore ferrichrome. In addition, FhuA also serves as a transporter of the antibiotics albomycin and rifamycin, as a receptor for the antimicrobial peptide microcin J25 (MccJ25), a number of bacteriophages, including T1, T5, and φ80, and the protein toxin colicin M. Furthermore, the dynamics of the WT-FhuA protein at an atomistic level has been revealed by molecular dynamics simulations. The FhuA channel exhibits a remarkable robustness, versatility, tractability, and thermal stability, as documented by prior spectroscopic and calorimetric studies.

As described in greater detail below, FhuA was bioengineered via a series of single domain or multiple loop deletions to investigate which parts of the FhuA protein contribute to the occlusion of the lumen. First, a deletion mutant was constructed to remove the cork domain, which encompassed the first 160 amino acids (FhuAΔ1-160) (see TABLE 1). Second, 52% of strand 138 was deleted along with nine amino acids of loop L4 (FhuAΔ335-355). Third, 52% of strand 138 along with most of loop L4 (FhuAΔ322-355) was deleted, leaving the first seven amino acids. Note that this construct will not have loop L4 deleted per se, but it might put a structural constraint on loop L4 to compensate for the loss of the majority of the β strand in the barrel. Loop L4 was targeted for modifications because it has been shown to reduce the extracellular entrance to the lumen of FhuA protein by approximately 50%, and perhaps it would prevent more modulation or even the release of the cork upon the application of a transmembrane potential. Further, in addition to single-deletion FhuA mutants, double and multiple deletion mutants were examined in order to obtain a comprehensive picture of the cumulative effect of both the cork domain and several large extracellular loops on the biophysical features of the FhuA protein.

Figure 2:
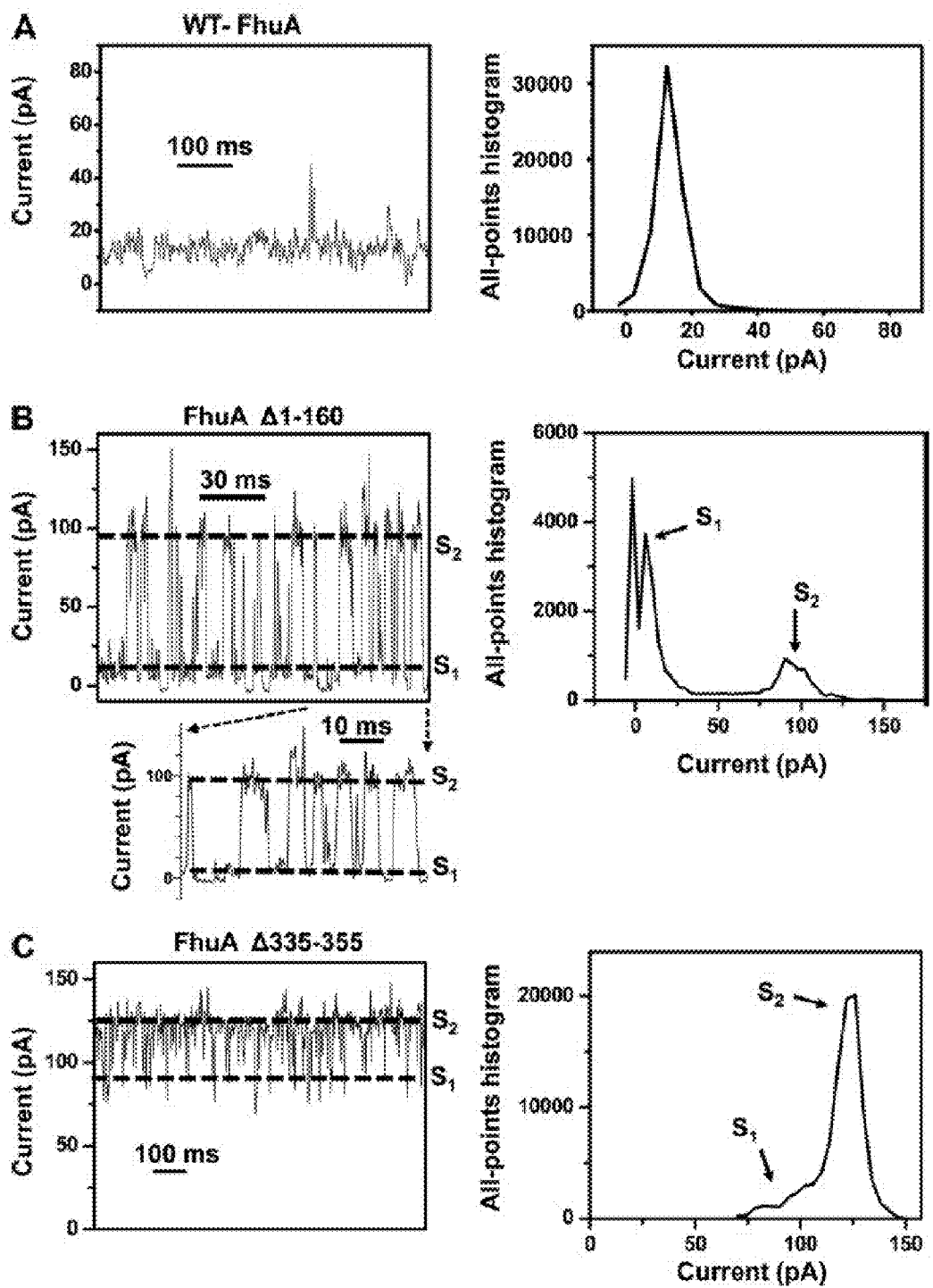
FIG. 2 shows representative graphs of single-channel electrical recordings with WT-FhuA and single-deletion mutants of the FhuA protein.
Figure 3:
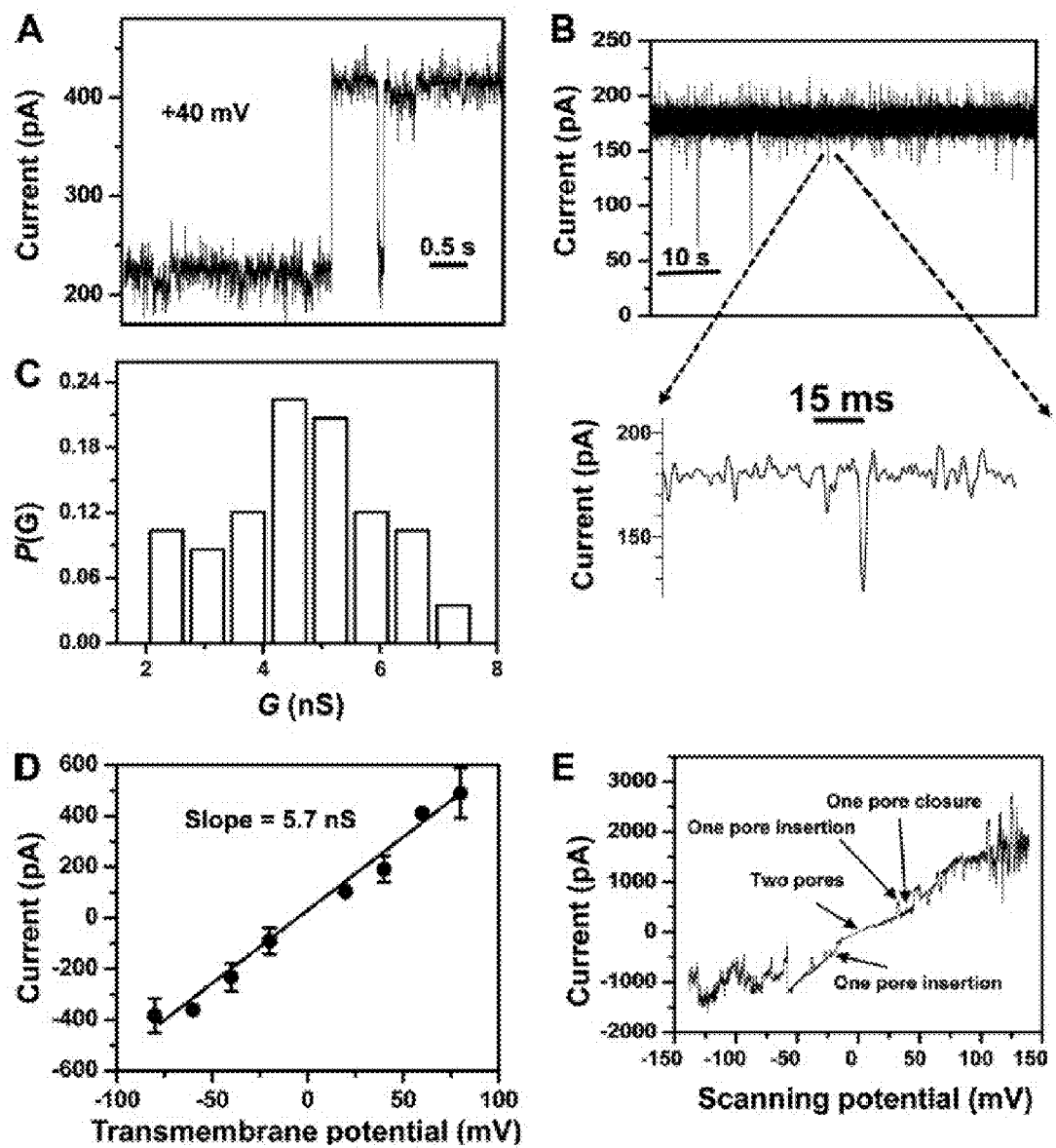
FIG. 3 shows graphs of single-channel electrical recordings of membrane-extracted FhuA ΔC/Δ4L ("mFhuA ΔC/Δ4L") protein.
Figure 4:
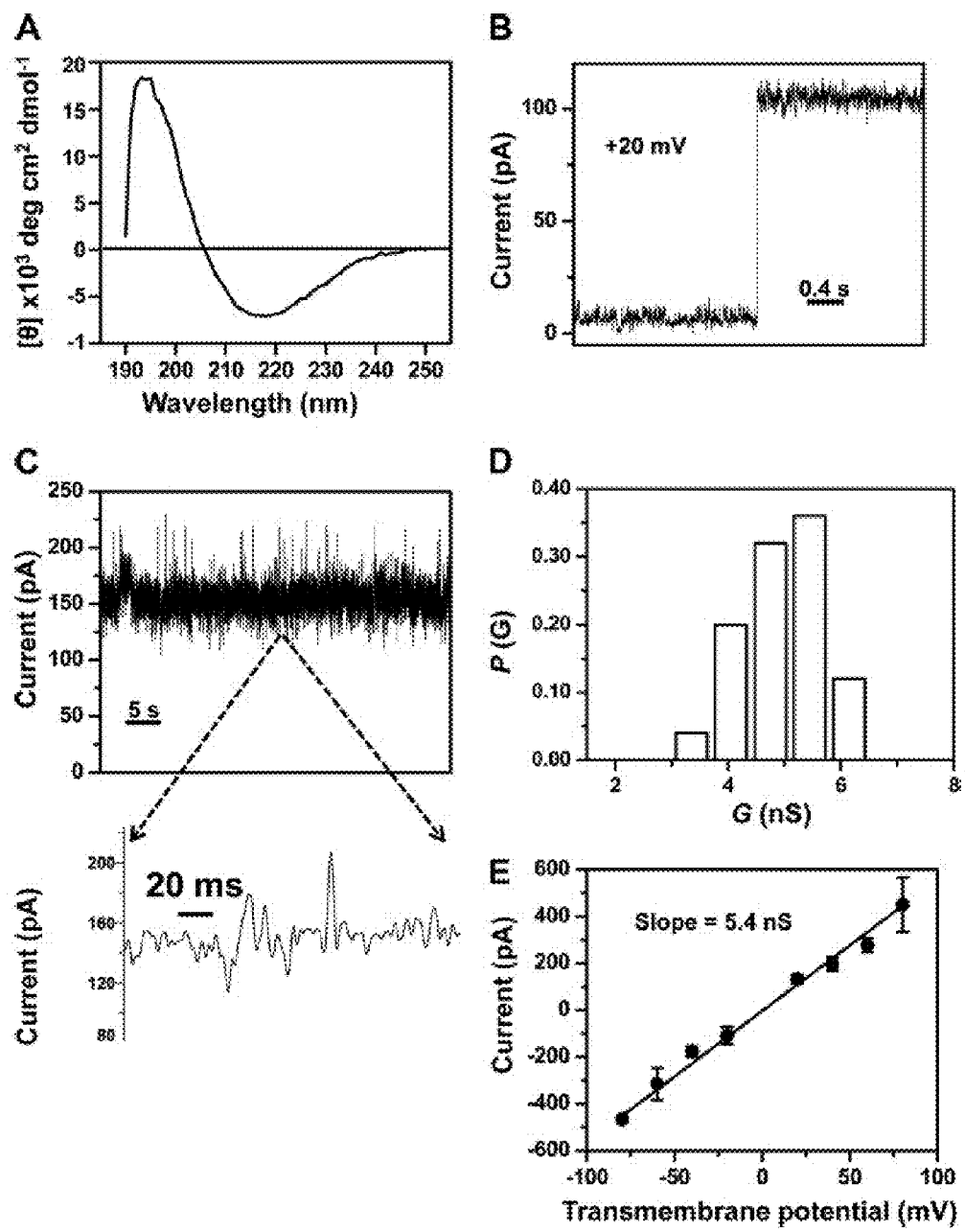
FIG. 4 shows graphs of single-channel electrical recordings of refolded FhuA ΔC/Δ4L ("rFhuA ΔC/Δ4L") protein.

For example, it is shown herein that the FhuA Δ1-160 protein pore exhibits a signature decorated by a highly dynamic behavior, featuring current fluctuations between a large conductance (~2.5 nS), open sub-state, $S_2$, and a low conductance (~0.2 nS), partly closed sub-state, $S_1$ (FIG. 2B). This finding indicates that there is an abrupt alteration of the ion flow across the cork-free FhuA protein channel. Similar results were found with the plug-free mutant of the PapC usher protein channel, a 24-stranded β-barrel membrane protein. These transitions are not caused by collapse of the β barrel due to the lacking support of the cork, since they were never observed with the engineered FhuA ΔC/Δ4L protein pore (FIGS. 3 and 4).

Figure 5:
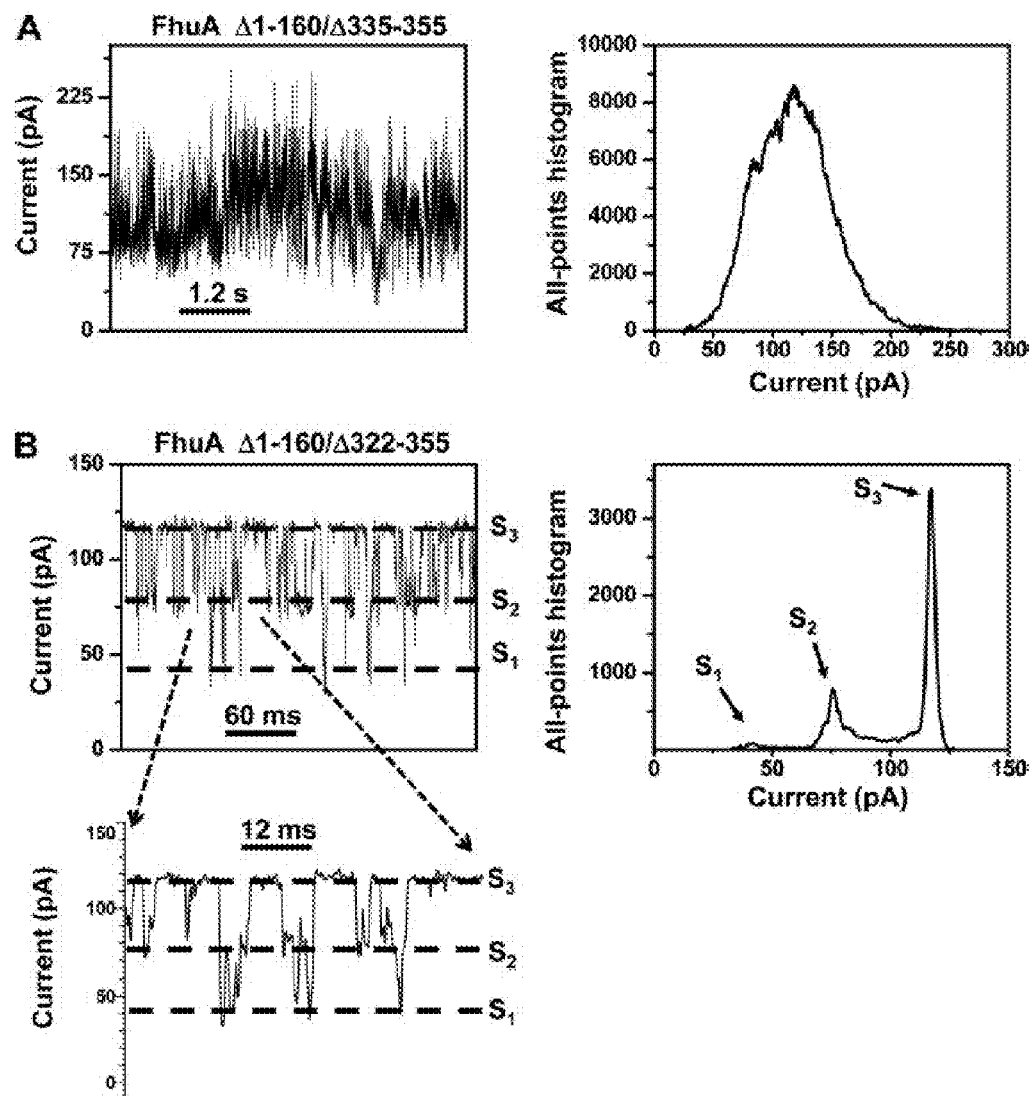
FIG. 5 shows representative graphs of single-channel electrical recordings of FhuA Δ1-160/Δ335-355 (A) and FhuA Δ1/Δ322-355 (B) proteins.

It was also observed that the fluctuations between the $S_1$ and $S_2$ sub-states of the cork-free FhuAΔ1-160 protein had a current amplitude of ~2.3 nS (FIG. 2B). However, the cork-containing FhuA Δ335-355 protein pore exhibited frequent current fluctuations of ~1 nS (FIG. 2C). In addition, the cork-free FhuA Δ1-160/Δ335-355 protein pore showed current fluctuations between $S_3$ and $S_2$ sub-states of ~1 nS (FIG. 5B). These experimental findings suggest that loop L4 is involved in the gating dynamics of the cork-free FhuA Δ1-160 protein channel. This hypothesis is also supported by the structural observations that this loop has a capping role in keeping the cork domain within the pore lumen.

The modifications resulted in a ~33% reduction in the number of amino acids in the final channel-forming protein which had a measured conductance of ~3.9 nS. When reconstituted into a synthetic bilayer, the protein nanopore was capable of sensing large polypeptides and discriminating between modified protein analytes.

By the systematic deletion of additional long and flexible extracellular loops (L3, L5, and L11), an open and stable protein channel was obtained, which is characterized by the largest single-channel conductance (~4.9 nS) ever measured with an engineered FhuA protein. Remarkably, the electrical recordings with mFhuA ΔC/Δ4L and rFhuA ΔC/Δ4L revealed closely similar average unitary conductance values (FIGS. 3, A and B, and 4, B and C). However, the mFhuA ΔC/Δ4L proteins exhibited a broader distribution in single-channel conductance (FIGS. 3C and 4D).

In summary, a monomeric β-barrel protein is successfully engineered, which forms large conductance and stable single channels in planar lipid bilayer, as judged by high resolution electrical recordings. It is shows that it is possible to radically redesign an outer membrane protein with a highly distinct functionality from the native protein. This newly redesigned monomeric protein can be easily altered by engineering targeted functional groups at strategic positions within the interior of the pore. Therefore, FhuA serves as a versatile model for exploring the folding and stability of integral membrane proteins and their relationship to the mechanisms of gating dynamics and ion conductance. The WT-FhuA protein is meant to prevent the passage of small molecules except under specific energy-dependent conditions. In contrast, the large conductance FhuA ΔC/Δ4L protein channel, with the cross-sectional sides of 3.1×4.4 nm, is conceivably "translocation-competent" for bulky biopolymers. Certainly, the FhuA ΔC/Δ4L protein pore might serve as a natural scaffold for the design and development of nanopore-based sensing elements. For example, electrostatic and hydrophobic groups can be engineered at desired positions within the pore lumen with atomic precision. From a technical point of view, it is also shown that by utilizing two distinct extraction and purification procedures, detergent-assisted membrane extraction and refolding from inclusion bodies, an engineered FhuA ΔC/Δ4L protein with a closely similar large single-channel conductance but a slightly different electrical signature is obtained. Moreover, customized and redesigned FhuA proteins with well defined biophysical, biochemical, and structural features might also be used in gene delivery, drug loading, and encapsulation techniques for medical biotechnology.

The experimental design and rational engineering of the FhuA protein can translate to other proteins, leading to novel protein configurations and uses. It is anticipated that these engineered protein pores will have a profound impact in the realm of nanopores, with a particular emphasis in medical biotechnology.

EXAMPLE 1

Engineering the FhuA Proteins

The FhuA protein meets the criteria for an ideal protein for engineering an open stable pore; it is a monomeric, β-barrel protein with a lumen of (3.6 nm×4.1 nm). See, for example, FIG. 1. See also, TABLE 2, which is a comparison of the conductance and oligomeric state of FhuA ΔC/Δ4L pore and other engineered pores, where the measured conductance for the FhuA ΔC/Δ4L pore was obtained from a total of 93 insertions (conductances for other pores and all inner dimensions were obtained from respected references, and all pores were engineered to give the reported conductances with 1 M KCl containing buffers). The oligomeric state in TABLE 2 constitutes how many subunits make up the pore, and the hemolysin units are a relative scaling to hemolysin pore diameter (X/αHL), where X is the diameter of the measured nanopore. Lastly in TABLE 2, the conductance of MspA pore is higher than related pores in dimensions because its length is 1 nm.

TABLE 2

Comparison of conductance and oligomeric state of the FhuA Δ4L pore with other engineered pores.

| Protein pore | Pore diameter (nm) | Conductance (nS) | Oligomeric state | Hemolysin Units (HU) |
| --- | --- | --- | --- | --- |
| αHL | 1.4 | 0.9 | 7 | 1 |
| Phi29 connecter | 3.6 | 4.8 | 12 | 2.6 |
| MspA | 1 | 4.9 | 8 | 0.7 |
| OmpG | 1.4 | 1.2 | 1 | 1 |
| FhuA | 3.9 | 3.85 | 1 | 2.8 |

Figure 6:
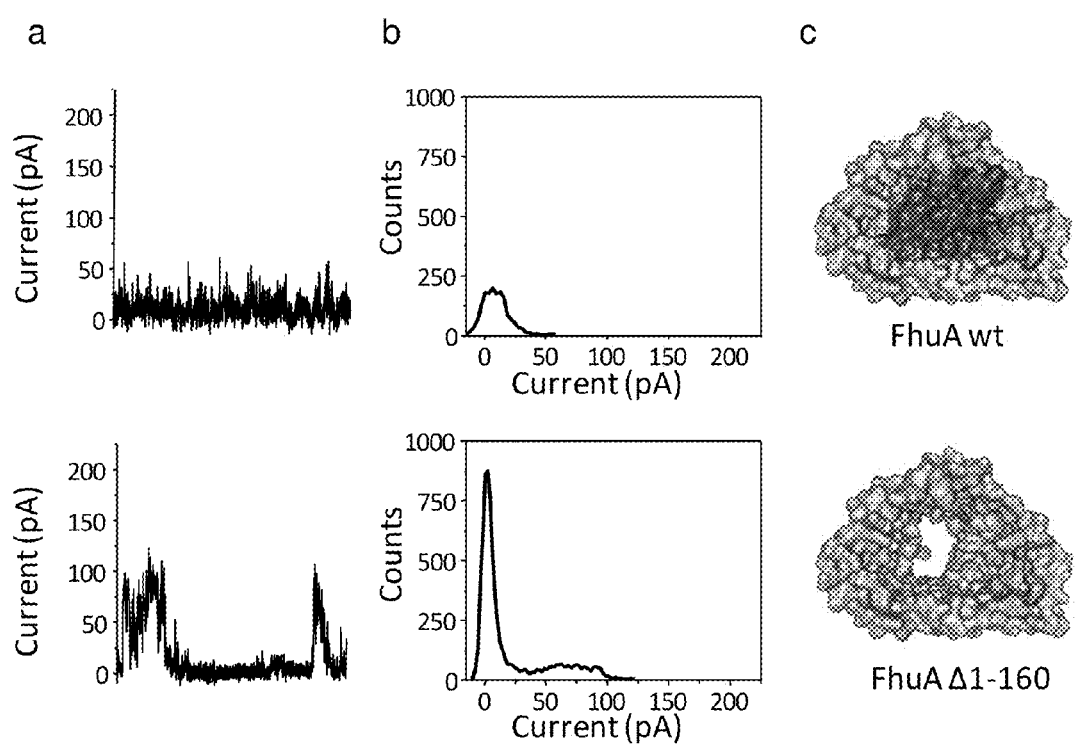
FIG. 6 is: (A) a graph of representative single-channel electrical recordings of WT-FhuA (top) and FhuA Δ1-160 (bottom) in 10 mM potassium, 1M KCl, phosphate buffer, pH 6.0; (B) a graph of all-point amplitude Gaussian histograms used for the determination of the most probable open-state conductance of the channel; and (c) cartoon representations of protein structure with surface presentations for WT-FhuA and FhuA Δ1-160 viewed from the periplasmic side (cis)

Earlier studies of the FhuA protein suggest that the protein can form an open pore, as these studies show channel openings at the macroscopic level. Some of the studies were conducted prior to the solving of the crystal structure of FhuA and thus resulted in engineered proteins in which some parts of the β barrel were removed, or in a combination with removing these parts of the β barrel along with the occluding cork (Δ 1-160). These constructs included FhuA Δ1-160, FhuA Δ5-160, FhuA Δ5-160/Δ335-355, FhuA Δ322-355, and FhuA Δ335-355. In an attempt to gain insights of these constructs at a single-channel resolution, these constructs were expressed and single-channel recordings were performed to examine their pore-forming activity. None of these constructs gave the desired stable open pore at the single-channel resolution in the current experimental conditions, specifically, the FhuA cork mutant (Δ1-160) did not form open channels, as shown in FIG. 6. This construct, based on the crystal structure, was expected to give a hollow pore while maintaining the β-barrel structure, as shown in FIG. 1. It was hypothesized that the failure of obtaining an open stable pore using this mutant is that the extracellular loops on the cis side fold back into the lumen during an applied potential resulting in blocking the otherwise open hollow pore.

The following four loops were identified for modification: L3, L4, L5, and L11, as shown in FIG. 1. These loops were chosen based on their length and spatial orientation in the FhuA crystal structure. To prevent these loops from folding back into the lumen, it was decided to delete the four loops and replaced them with the short turn NSEGS (SEQ. ID NO: 10) to lessen the structural limitations in the β-barrel formation. To ensure purification homogeneity, a C-terminal 6×His$^+$ connected by a thrombin cleavage sequence was then added. The resulting gene was named fhua ΔC/Δ4l. The FhuA ΔC/Δ4L protein was purified from the outer membrane through selective detergent and differential centrifugation purification methods, however the yield was not satisfactory as most of the expressed proteins went to inclusion bodies (data not shown). Advantageously, the inclusion bodies were used to purify the protein under denaturing conditions (see FIG. 7A), and the refolded proteins were then obtained by dilution in solution containing micelles to give quantitatively reliable amount of proteins for single-channel recordings.

EXAMPLE 2

Pore-Forming Activity of FhuA Δ4L

Figure 7A:
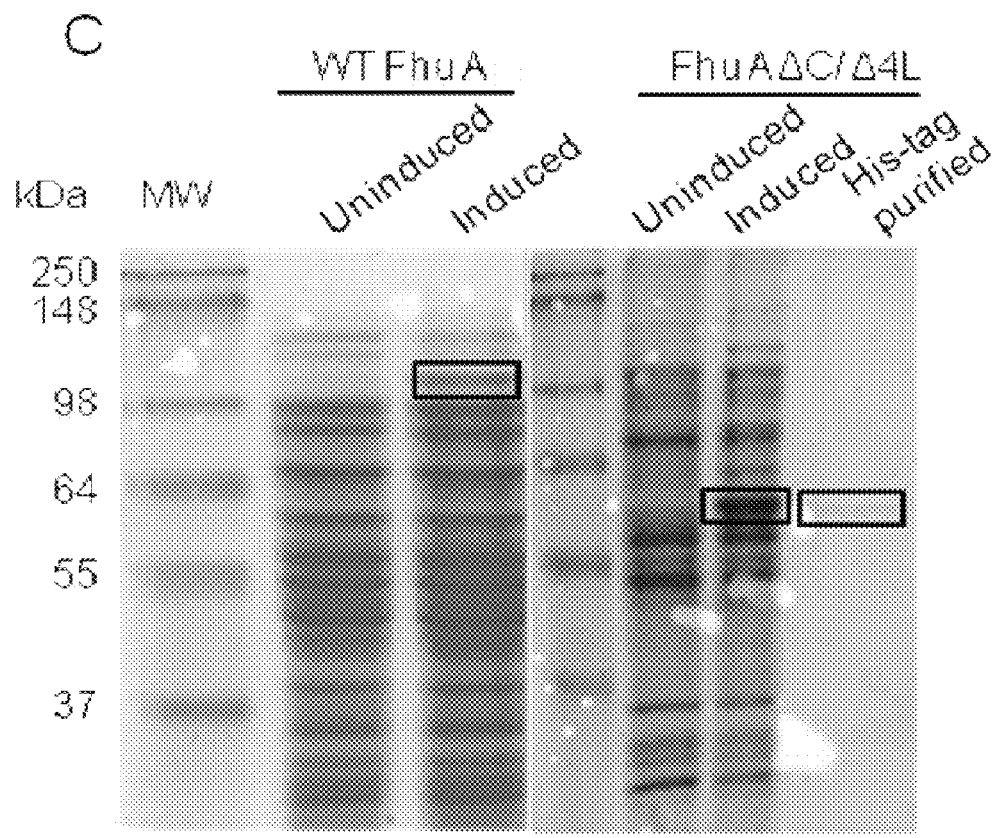
FIG. 7A is an SDS-PAGE indicating the purity of purified FhuA ΔC/Δ4L pore and its ~30 reduction in molecular weight in comparison to WT-FhuA.
Figure 7B:
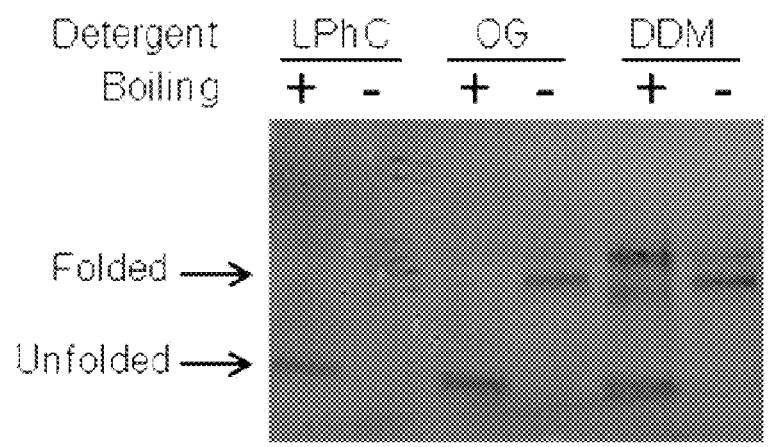
FIG. 7B is an image of an SDS-PAGE gel depicting the results of a heat modifiability assay for the refolded FhuA ΔC/Δ4L protein.

In this work, a simple rapid-dilution protocol is used. Using this protocol, the denatured, affinity-purified FhuA ΔC/Δ4L protein was diluted in buffer solution that contained n-dodecyl-β-D-maltopyranoside ("DDM"), n-octyl-β-D-glucopyranoside ("OG") or 1-lauroyl-2-hydroxy-sn-glycero-3-phophocholine ("LPhC") detergent. The engineered FhuA ΔC/Δ4L protein exhibited heat modifiability in its electrophoretic mobility on SDS-PAGE gel, suggesting that they acquired properties of refolded β-barrel proteins (FIGS. 7A and 7B). Similar findings were not obtained using other detergents, such as Zwittergent 3-14 and N,N-dimethyldodecylamine-N-oxide ("LDAO"), because the proteins became insoluble in aqueous phase.

Figure 8:
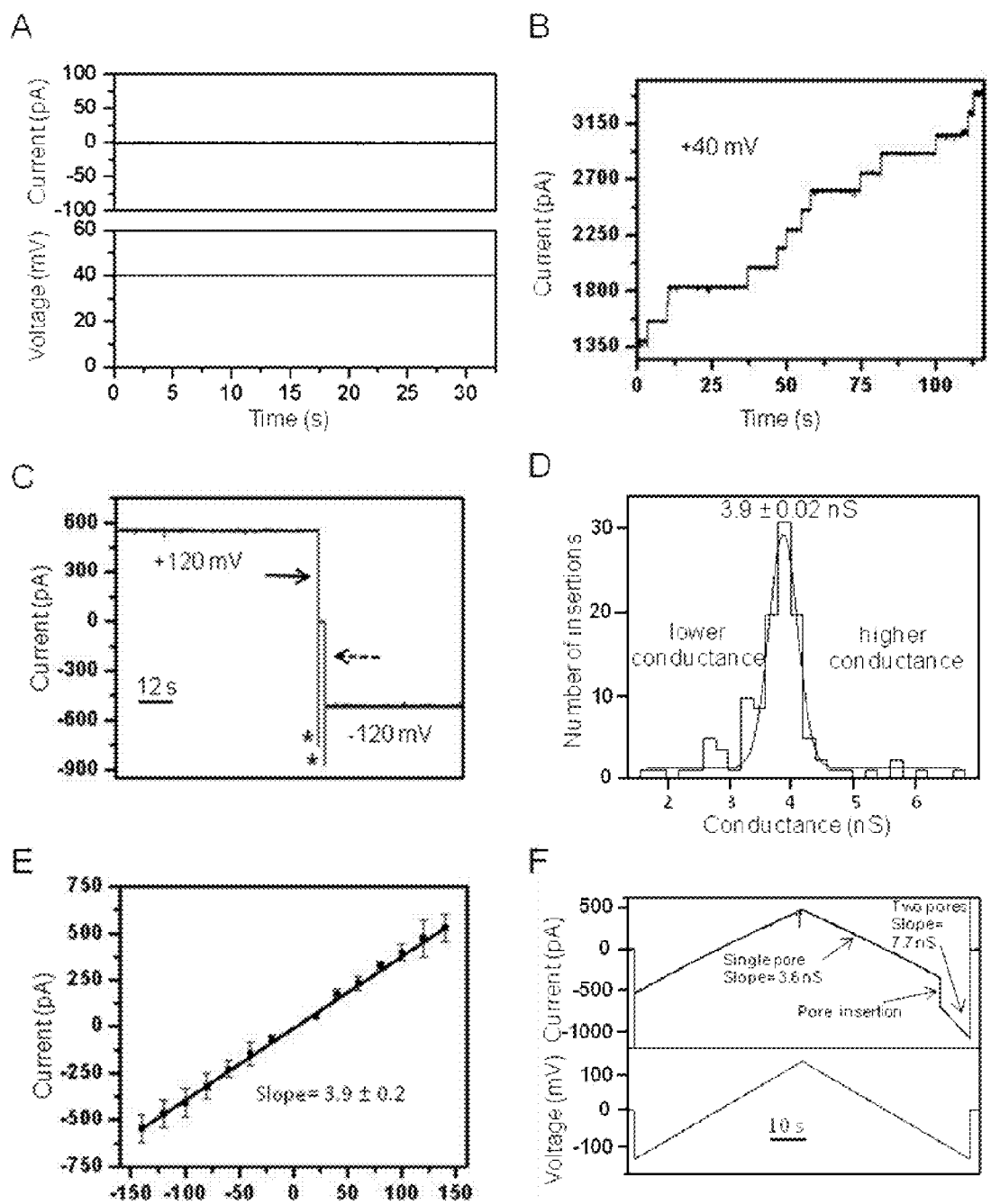
FIG. 8 is: (A) an electrical signature of the synthetic bilayer formed on a ~50 μm aperture in 1 M KCl, 10 mM potassium phosphate, pH 7.4 and in the presence of 0.01% DDM, with an applied transmembrane potential of +40 mV; (B) insertions of single channels in the bilayer after the addition of 150 ng refolded FhuA ΔC/Δ4L proteins at an applied transmembrane potential of +40 mV; (C) a single-channel recording at an applied potential of +120 mV and −120 mV; (D) a histogram of the distribution of single-channel conductance values of the FhuA ΔC/Δ4L protein nanopores at an applied transmembrane potential of +40 mV; (E) the relationship between current and voltage of single protein nanopores (I/V curve); and (F) voltage ramps of one and two protein nanopores.

High-resolution single-channel electrical recordings were used to examine the properties of the engineered FhuA ΔC/Δ4L protein nanopore. Addition of detergent into the chamber, up to ~0.01% LPhC, OG, or DDM, did not influence the stability or the insulating nature of the synthetic bilayer (FIG. 8A). Upon its addition to the chamber, the engineered FhuA ΔC/Δ4L protein nanopore showed a pore-forming activity, as evidenced by the discrete, stepwise increase in membrane conductance (FIG. 8B).

Figure 9:
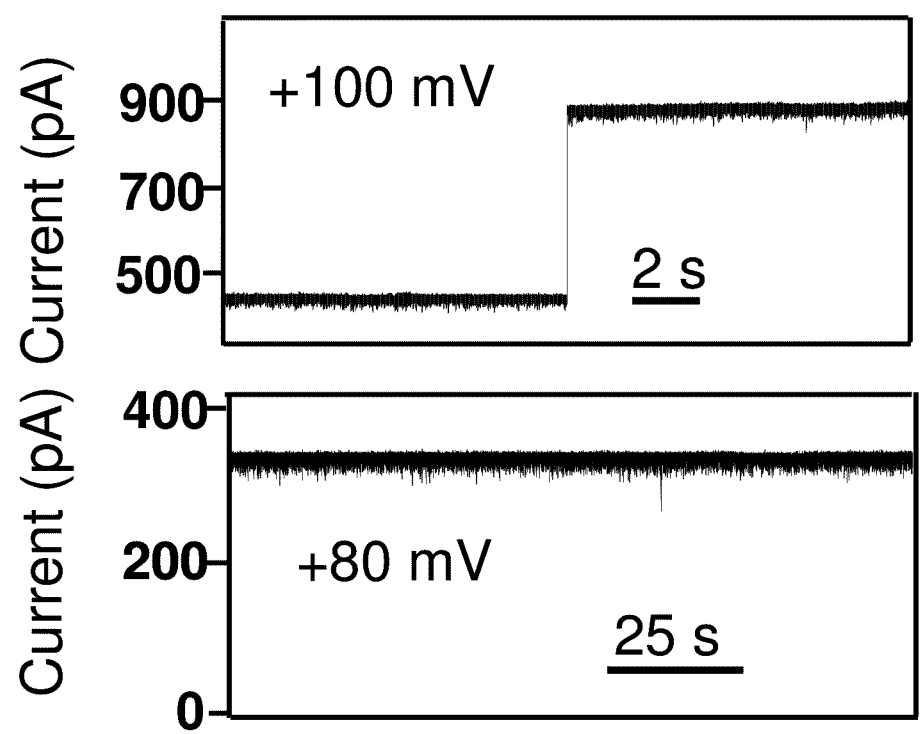
FIG. 9 is graph of a single-channel insertion at an applied potential of +100 mV (top panel), and a single-channel recording an applied potential of +80 mV (bottom panel)
Figure 10:
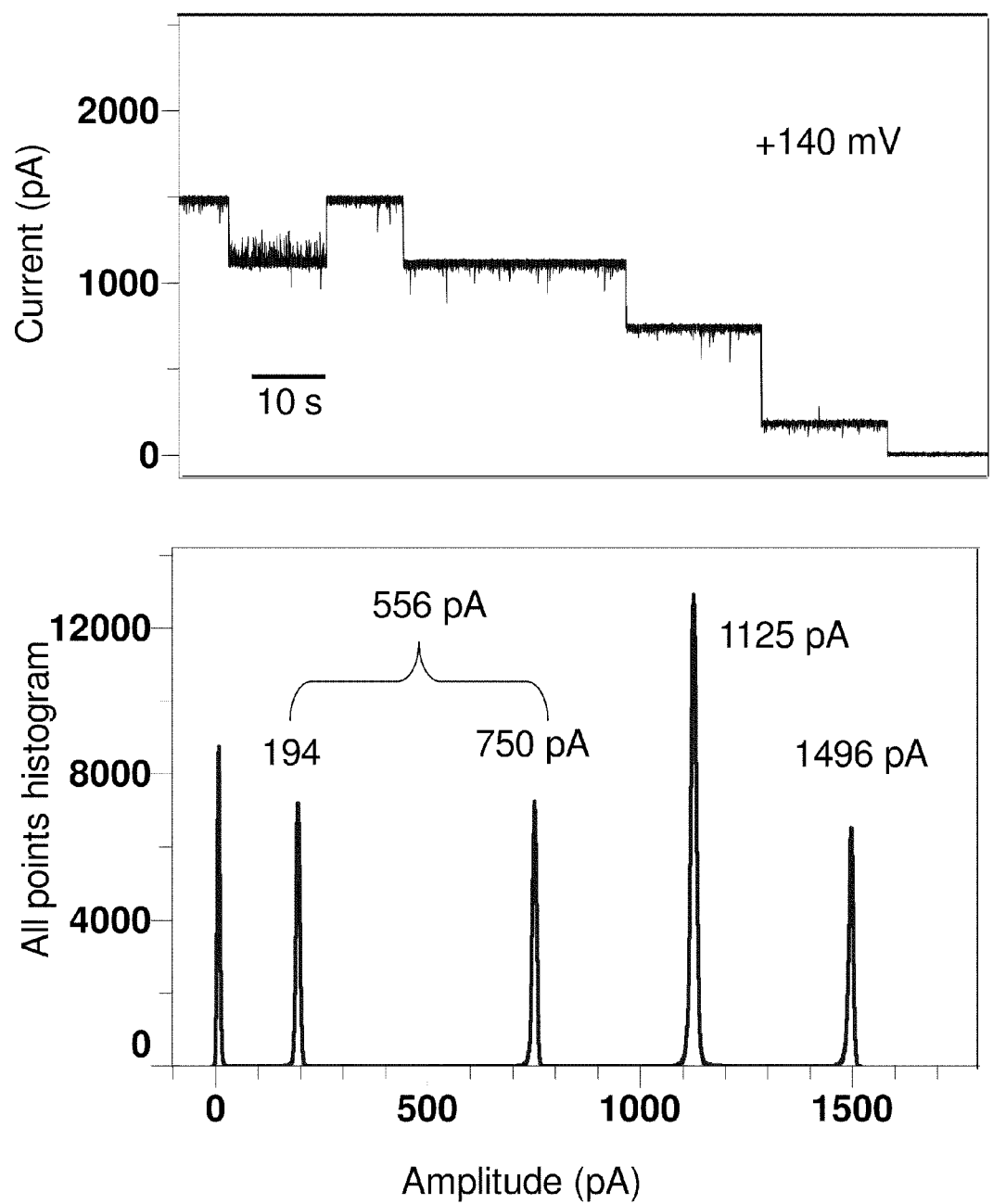
FIG. 10 is: (A) a graph of stepwise closures of FhuA ΔC/Δ4L channels at an applied potential of +140 mV (top); and (B) an all-points histogram showing the current reduction in each channel closures, with recordings taken in 10 mM potassium, 1M KCl, phosphate buffer, pH 7.4 and filtered at 2 kHz.

These inserting channels are stable at the applied potential of +100 mV, as shown in FIG. 9 (upper panel). Further, single channels can stay open for long period of time, with unresolvable current deflections and very infrequent ($8.5 \times 10^{-3}$ s$^{-1}$) current reductions of ~15-25%, as shown in FIG. 9 (lower panel). Two lines of evidence verified that a single pore causes the single insertion. First, at higher applied potential an infrequent (<1%) step-wise decrease in current was observed which is almost equal to current jump during single pore insertion, as shown in FIG. 10. Second, the addition of analytes caused a current reduction in single-channel recordings by ~95%.

The engineered FhuA ΔC/Δ4L protein nanopore was refolded using DDM, OG and LPhC, and the single-channel recordings showed a similar unitary conductance (TABLE 2). The single-channel data obtained with DDM is shown herein. The unitary current, in 1 M KCl, 10 mM potassium phosphate, pH 7.4, was 156±21 pA at an applied potential of +40 mV, which corresponded to a single-channel conductance of ~3.9±0.5 nS (n=92, FIG. 8B, TABLE 2). Spontaneous insertions of the FhuA ΔC/Δ4L protein nanopores required neither an osmotic gradient nor supplementary preparative steps, such as reconstitution into proteoliposomes. This engineered protein nanopore is stable at the applied potential of 120 mV (FIG. 8C). Furthermore, the FhuA ΔC/Δ4L protein nanopores maintained their open state for long periods, in the range of tens of minutes. The distribution of the values of unitary conductance showed a Gaussian with a peak at ~3.9 nS (FIG. 8D). According to the X-ray crystal structure of the native FhuA protein, the cross-sectional area of the engineered cork-free FhuA protein nanopore is elliptical and has the average dimensions of 2.6×3.9 nm (including the side chains of the residues) (FIG. 1). Single-channel recordings employing a 40-kDa dextran polymer suggested that the average cross-sectional diameter of the FhuA ΔC/Δ4L protein nanopore is ~2.2 nm. This result was obtained by measuring the contribution of the pore's access resistance to the total resistance of the FhuA ΔC/Δ4L protein nanopore. The effective diameter of the nanopore was calculated assuming that FhuA ΔC/Δ4L is a simple non-selective cylinder at 1 M KCl.

The insertion of a single FhuA ΔC/Δ4L pore into the bilayer which resulted in an increase in the current of approximately 175±20 pA (N=8, equivalent to 4.3 nS) at a potential of +40 mV in 10 mM phosphate buffer 1 M KCl, pH 7.4 was routinely observed. However, lower and higher conductances were also observed with an occurrence of 5% and 2% respectively, as shown in FIG. 8D.

To reliably measure the conductance of the pore, the slope from the voltage versus current plot was derived, which gives 3.9±0.2 nS in 1 M KCl, 10 mM potassium phosphate, pH 7.4 (FIG. 8E). The data were derived from at least 5 distinct experiments, and using two different protein preparations. In addition, single-channel electrical recordings were performed with a single FhuA ΔC/Δ4L protein nanopore under a voltage ramp, using the same experimental conditions (FIG. 8F). It was discovered found that the slopes of the fitted curve provided values of ~3.6 nS and ~7.7 nS for a single nanopore and two nanopores, respectively. Moreover, the FhuA ΔC/Δ4L protein nanopores exhibit a stable and quiet single-channel electrical signature at applied transmembrane potentials in the range between −140 and +140 mV (FIG. 8F), in contrast to other large transmembrane pores that adopt a β-barrel structure, such as the voltage-dependent anion channel (VDAC) and the PapC usher.

Figure 11:
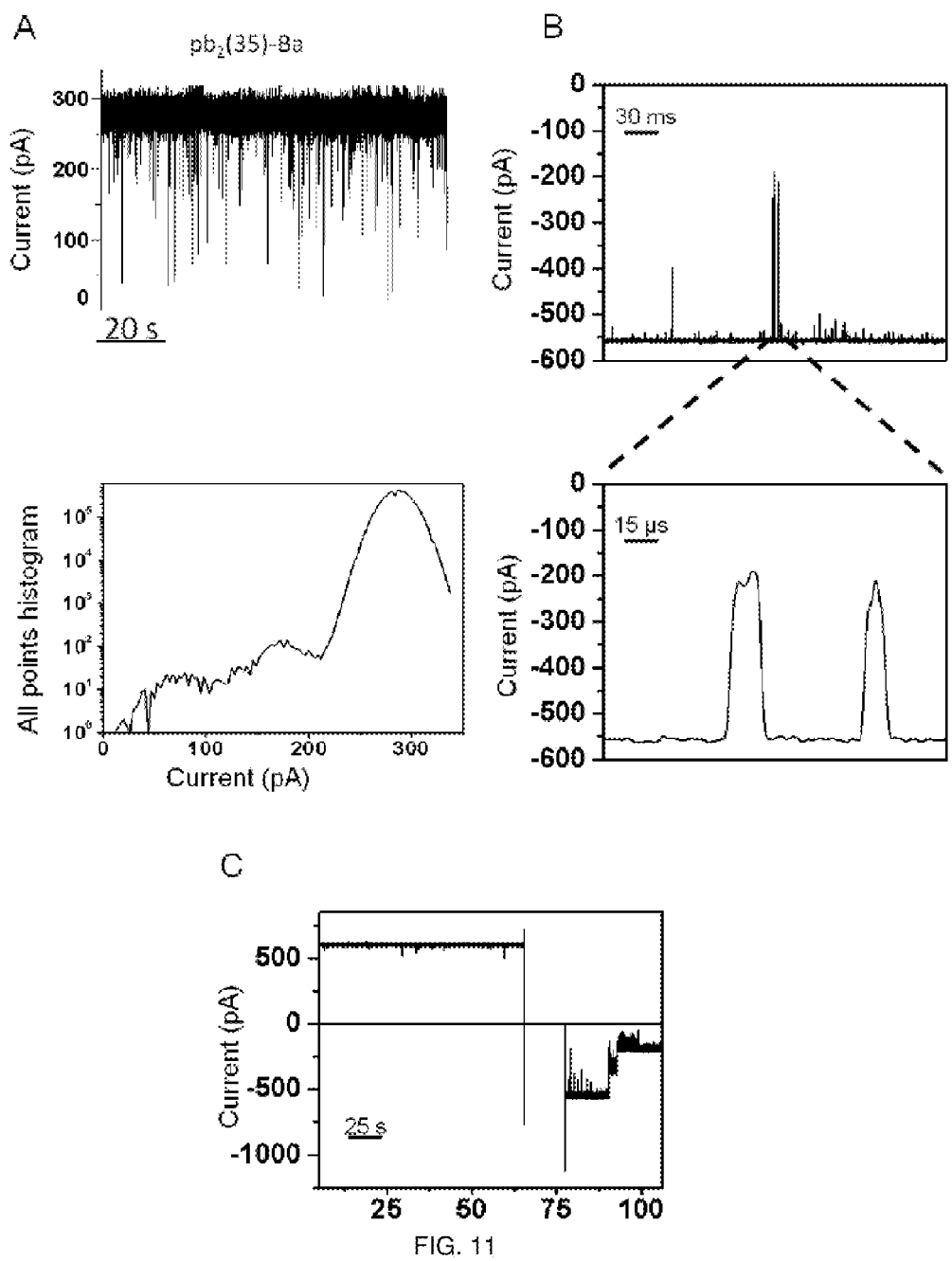
FIG. 11 is: (A) a single-channel recording showing transient single-channel current blockades made by barnase protein fused to positively-charged presequence $pb_2(35)$ ($pb_2$ (35)-Ba); (B) a graph of transmembrane potential; and (C) representative single-channel recordings of FhuA ΔC/Δ4L.

The transient single-channel current blockades made by long polypeptide chains are up to 95% of the unitary current of the engineered protein (FIG. 11A), suggesting that the nanopore inserts into a planar lipid bilayer as a monomer. Further, at very high transmembrane potentials (≥140 mV), the voltage-induced spontaneous closures of the FhuA ΔC/Δ4L protein nanopores show values of residual current that are smaller than 50% of the unitary current (FIG. 11B). This engineered protein nanopore inserts in a single orientation. For example, at an applied transmembrane potential of 140 mV, the voltage-induced gating of the single-channel current was always dominant at a negative bias (FIG. 11C).

Figure 12:
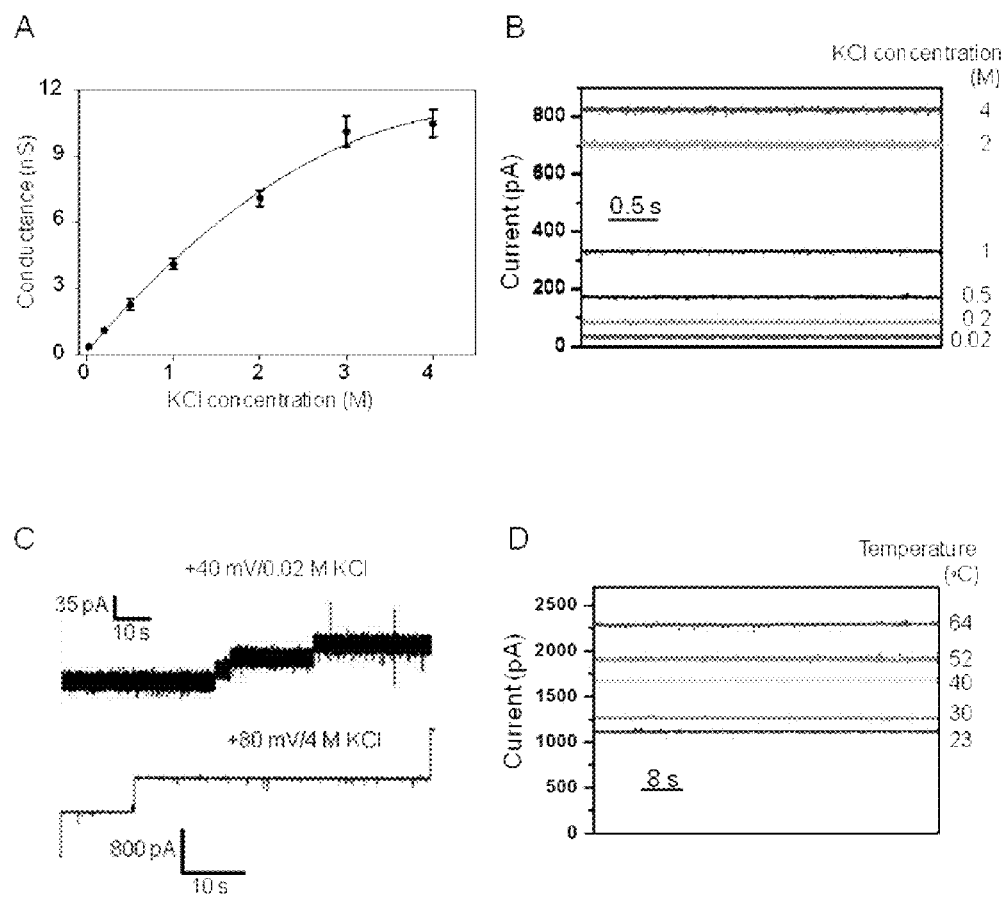
FIG. 12 is: (A) a graph of single-channel conductance of the FhuA ΔC/Δ4L protein nanopore as a function of the KCl concentration; (B) a graph of single-channel current traces acquired with FhuA ΔC/Δ4L protein nanopore at various KCl concentrations, and in 10 mM potassium phosphate, pH 7.4; (C) a graph of FhuA ΔC/Δ4L pore inserts efficiently into a lipid bilayer at low (the top trace) and high (the bottom trace) KCl concentrations; and (D) electrical traces with the current made by three distinct FhuA ΔC/Δ4L protein nanopores at various temperatures and in 1 M KCl, 10 mM potassium phosphate, pH 7.4.
Figure 13:
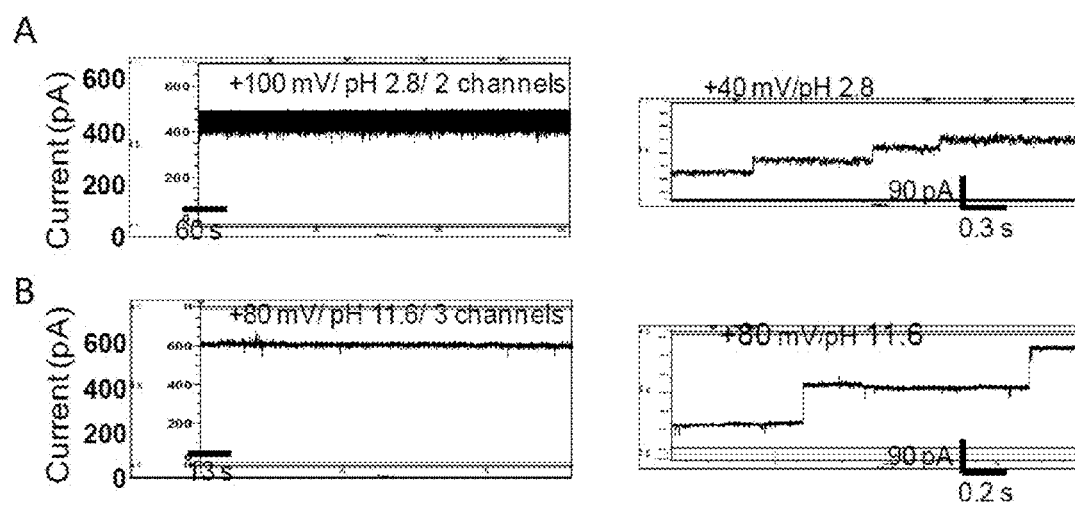
FIG. 13 is: (A, left panel) an electrical recording with two channels at an applied potential of +100 mV; (A, right panel) stepwise single-channel insertions at an applied potential of +40 mV; (B, left panel) an electrical recording with three channels at an applied potential of +80 mV; and (B, right panel) stepwise single-channel insertions at an applied potential of +80 mV.

Critically important for this work and future applications, it was discovered that the engineered FhuA ΔC/Δ4L protein nanopore maintained its rigidity under a broad range of conditions. FIG. 12A presents the dependence of the single-channel conductance on the KCl concentration. The quiet signature of the single-channel current was observed in a wide range of the KCl concentration, between 20 mM and 4 M (FIG. 12B). In contrast, even in the case of the champion of barrel rigidity and quietness, the staphylococcal α-hemolysin (αHL) nanopore, a KCl concentration lower than 200 mM induces spontaneous and frequent gating events. The FhuA ΔC/Δ4L protein nanopore readily inserted into a planar lipid bilayer for all ion concentrations inspected in this work (FIG. 12C). It was observed that the engineered FhuA ΔC/Δ4L protein nanopore maintained its open state for long periods at temperatures up to 65° C. (FIG. 12D). Moreover, the FhuA ΔC/Δ4L protein nanopore remained open and quiet at pH 2.8 when the applied transmembrane potential was +100 mV, and at pH 11.6 when the applied potential was +80 mV (FIG. 13). The FhuA ΔC/Δ4L protein nanopores also inserted into a synthetic lipid bilayer under highly acidic or alkaline pH as well (FIG. 13).

Among the potential large-diameter pores, the FhuA ΔC/Δ4L protein has many of the desired traits. First, FhuA ΔC/Δ4L channels are very stable and uniformly quiet at applied voltages between +140 and −140 mV, and do not show voltage-induced sub-states or conformations as compared to pneumolysin, VDAC, the PapC usher and others. Second, FhuA ΔC/Δ4L is monomeric in nature which gives FhuA ΔC/Δ4L a major advantage for future engineering and functionalization, in contrast to the recently engineered dodecameric phi29 motor protein, for example. Third, the large-scale expression, purification and preparation of FhuA ΔC/Δ4L makes this protein pore the logical choice for the fast production for future biotechnological applications. Moreover, FhuA ΔC/Δ4L does not need an intermediate step prior to insertion into the bilayer, as is required by other protein pores.

EXAMPLE 3

Single-Channel Electrical Signatures of the FhuA Protein and its Single-Deletion Mutants When the WT-FhuA protein was reconstituted into a planar lipid bilayer, a single channel conductance of 0.3±0.2 nS (n=4 distinct single-channel experiments) was observed at an applied membrane potential of +40 mV in 1 M KCl, 10 mM potassium phosphate, pH 7.4 (TABLE 3). FIG. 2A, left panel, shows a representative single-channel electrical trace recorded with the WT-FhuA protein. FIG. 2A, right panel, presents an all-points current amplitude histogram of the single-channel electrical trace illustrated in the left panel. This all-points current amplitude histogram identifies a current amplitude peak located at ~12.5 pA.

TABLE 3

Comparison of the Conductance Between Wt-FhuA Protein and the Deletion Mutants

| Protein | Conductance (nS) |
|---|---|
| WT-FhuA | 0.3 ± 0.2 (n = 4) |
| FhuA Δ1-160 | 2.5 ± 0.6 (n = 4) |
| FhuA Δ335-355 | 3.1 ± 0.2 (n = 3) |
| FhuA Δ1-160/Δ335-355 | 3.0 ± 0.5 (n = 3)[a] |
| FhuA Δ1-160/Δ322-355 | 3.0 ± 1.5 (n = 4)[b] |
| mFhuA ΔC/Δ4L | 4.8 ± 1.3 (n = 58) |
| rFhuA ΔC/Δ4L | 4.9 ± 0.7 (n = 25) |

Figure 14:
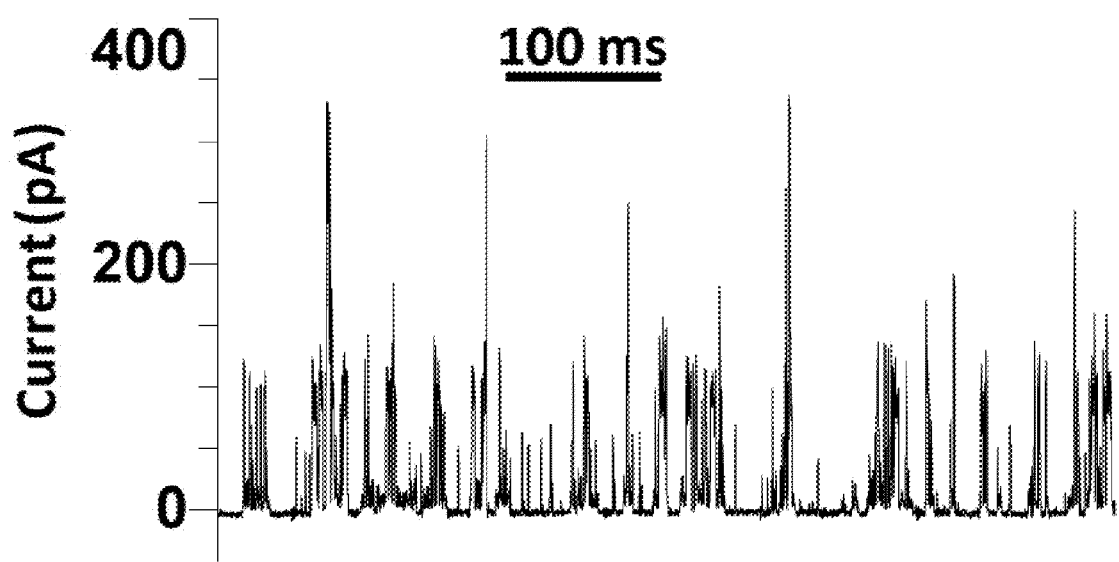
FIG. 14 is a graph of single-channel electrical recording with FhuA Δ1-160 protein.

To redesign an open FhuA protein pore, the cork domain was removed (FIG. 1). The expectation was that the removal of the cork domain should lead to a protein with a hollow lumen, forming a high conductance channel. Surprisingly, the single-channel current fluctuated between low conductance (0.2±0.1 nS, n=4) and high conductance (2.5±0.6 nS, n=4) current sub-states, $S_1$ and $S_2$, respectively (FIG. 2B and TABLE 3). Throughout this work, the assignment of different conductance sub-states relied on all-points current amplitude Gaussian histogram peaks (e.g. FIG. 2B, right panel). These two current sub-states are not generated from multiple channels but rather from one protein. If the trace observed with the FhuAΔ1-160 protein channel is produced by two different single-channel conductance proteins, then more independent small and large conductance openings of this mutant should have been observed. This is not the case. Instead, it was observed that $S_2$ occurred frequently after $S_1$. $S_1$ or $S_2$ were rarely noticed independently (0 to ~25 to 0 pA or 0 to ~100 to 0 pA, respectively). Taken together, it is likely that $S_1$ and $S_2$ are different open current sub-states of the same FhuAΔ1-160 protein pore. For example, the 5th last opening (FIG. 2B, expanded trace) is featured by a current amplitude that is the sum of the small and large opening. However, in this event, the current increases to the maximum value without having a discrete step at $S_2$. First, if this event was characteristic of the opening of two channels, it should show a discrete opening to the $S_2$ sub-state, followed by another low amplitude current step. This is not the case. Other closely similar events, but of greater current amplitude than the sum of the small and large opening, were noticed (FIG. 14).

Figure 15A:
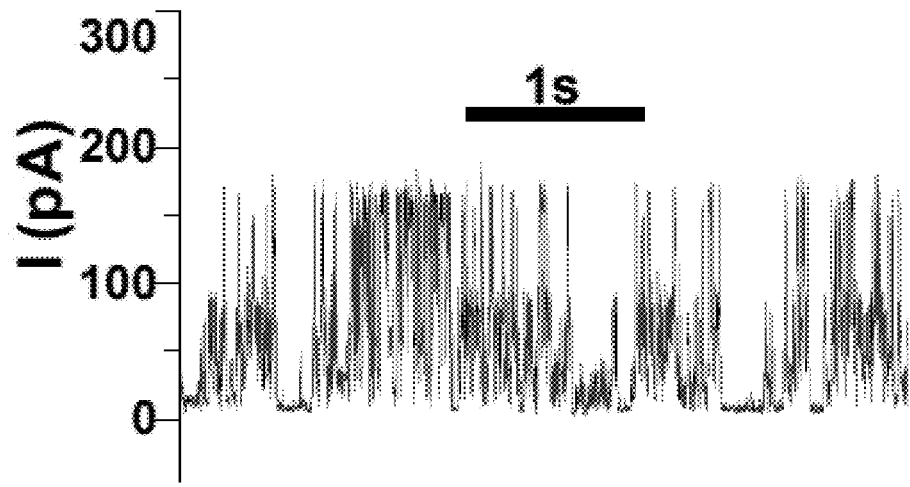
FIG. 15 shows graphs of: (A) representative single-channel electrical recording with FhuA Δ322-355; and (B) an all-point current amplitude histogram of 15A.
Figure 15B:
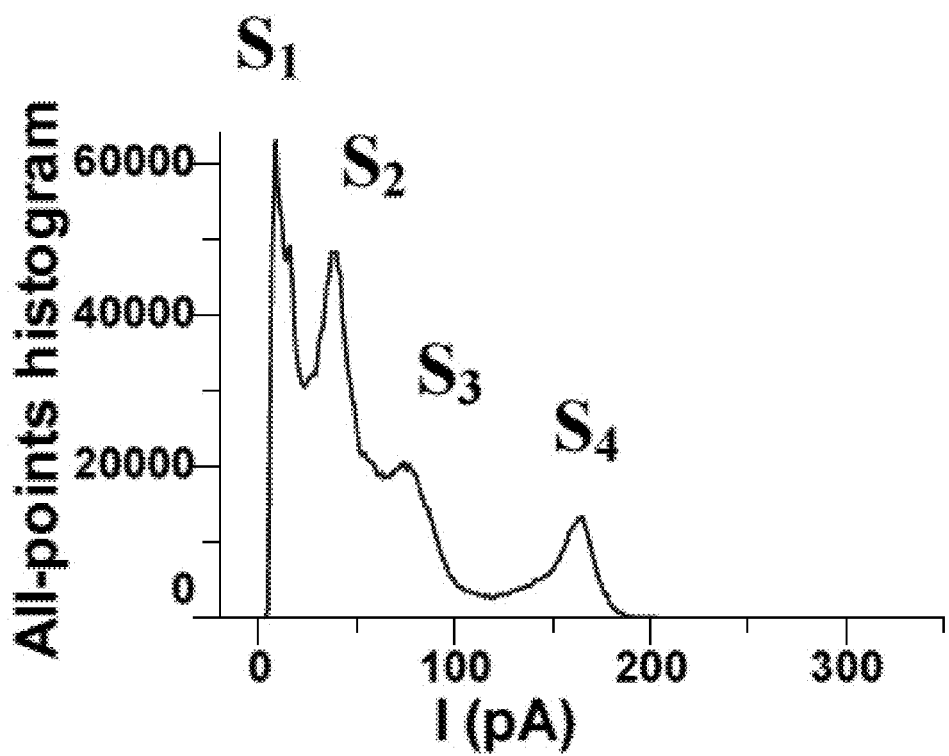

It has been shown, using macroscopic current measurements, that FhuA Δ335-355 exhibits an open pore. Therefore, this deletion mutant was examined using time-resolved single-channel electrical recordings. Specifically, it was desirable to determine whether the alteration of loop L4 impacts the gating fluctuations of the WT-FhuA protein (FIG. 1). Single-channel electrical recordings with the FhuA Δ335-355 protein agreed with the prior exploration of this mutant (38). FIG. 2C shows a representative single-channel electrical trace obtained with FhuA Δ335-355. This electrical trace reveals an open sub state $S_2$, with a single-channel conductance of 3.1±0.2 nS (n=3), accompanied by frequent short lived gating events reaching a current sub-state S1, with a single-channel conductance 1.9±0.2 nS (n=3). To obtain a better understanding of the current fluctuations produced by loop L4, the deletion mutant FhuA Δ322-355 was also examined. This mutant produces a channel with multiple open states within a very broad range of the single-channel conductance (FIG. 15). The observed maximum single-channel conductance was ~3.5 nS, indicating that further shortening of loop L4 results in a more fluctuating structure of the FhuA protein.

EXAMPLE 4

Single-Channel Electrical Signatures of the Double-Deletion FhuA Mutants

Analysis of the FhuA Δ1-160 protein indicated that the removal of the cork domain does not result in an open pore with a single unitary conductance. Furthermore, it is possible that loop L4 occludes the lumen. Therefore, the removal of both the cork domain (residues 1-160) and part of loop L4 (residues 335-355) was investigated. When FhuA Δ1-160/Δ335-355 was explored by electrical recordings, an open channel was observed with an average single-channel conductance of 3.0±0.5 nS (n=3) (FIG. 5A and TABLE 3), which is in accord with previous studies of this protein. In contrast to other FhuA derivatives examined in this work, the current noise is exceptionally high, whereas the current showed a "wavy" behavior (FIG. 5A). FIG. 5A shows a longer time scale of the trace to reveal the specific signature of this double-deletion FhuA mutant. Individual conductance substates could not be assigned to FhuA Δ1-160/Δ335-355. The all-points histogram was only used to extract the most probable current sub-state of this FhuA derivative. Similar to FhuA Δ1-160/Δ335-355, FhuA Δ1-160/Δ322-355 produces a channel with a single-channel conductance of 3.0±1.5 nS (n=4) (FIG. 5B and TABLE 3). The fundamental difference between FhuA Δ1-160/Δ335-355 and FhuA Δ1-160/Δ322-355 is the appearance of three discrete current sub-states of the latter protein channel (FIG. 5B), which undergoes transient closures with the following two dwell times: $\tau_1$=0.6±0.1 ms ($P_1$=0.37±0.01) and $\tau_2$=3.0±0.1 ms (P2=0.63±0.01) (n=4) and with the overall event frequency of 201±93 $s^{-1}$. Throughout this work, the fits were based upon log likelihood ratio tests, with a given confidence level of 0.95.

EXAMPLE 5

Single-Channel Electrical Signatures of the Membrane-Extracted, Multiple Deletion Mutant FhuA ΔC/Δ4L Inspection of the crystal structure of FhuA indicated that three additional loops can be folded back into the interior of the pore. Loops L3, L5, and L11 were identified for further modification. These loops were chosen based on their length and spatial orientation in the FhuA crystal structure (FIG. 1 and TABLE 1). Furthermore, our protein structure prediction for double-deletion mutants has shown that these loops significantly obstruct the entrance to the pore lumen. To prevent these loops from folding back into the pore lumen, the FhuA protein was redesigned with the following deletions: L3(residues Tyr243-Asn273), L5(residues Asp394-Asn419), L11 (residues Asn682-Arg704) along with L4 (residues Cys318-His339 ), and the cork domain (residues Met1-Pro160 ), leaving β-strand 8 unmodified. All loops were replaced with short turns, encompassing the sequence NSEGS (SEQ. ID NO: 10). The resulting engineered protein, called mFhuA ΔC/Δ4L, was extracted from the outer membranes of E. coli. The average cross-sectional surface and internal molecular volume of mFhuA ΔC/Δ4L are 8.64±103 $Å^2$ and 38.1±103 Å3, respectively, as calculated by using CASTp software. These estimates were made with the assumption that the remaining FhuA structure is unmodified by these major cork and loop deletions.

Figure 16:
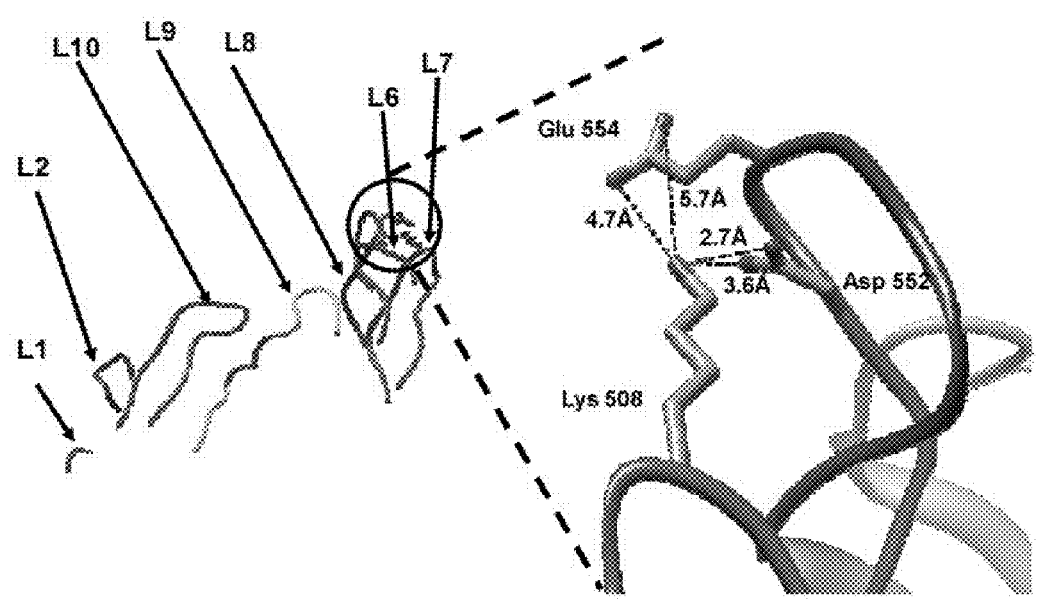
FIG. 16 shows cartoon presentations of: (left) the extracellular loops of the WT-FhuA protein; and (right) an expanded region of the network of ion-pair interactions formed between L7 and L8.

The remaining unmodified loops L1, L2, L6, L7, L8, L9, and L10 featured 3, 6, 4, 14, 8, 14, and 16 amino acids in length (TABLE 1), respectively. L1, L2 and L6 are very short, and unlikely do fold into the pore lumen (FIG. 16, left panel). Lys508 in L7 is involved in a network of ion-pair interactions with Asp552 and Glu554 in L8 (FIG. 16, right panel). Recently, it has been shown that these kinds of electrostatic interactions can stabilize the loops in a β-barrel protein pore. Therefore, it was anticipated that these ion-pair interactions would prevent L7 and L8 from folding back into the pore lumen. L9 is stretched out between two highly asymmetric β strands, making a rigid structure and perhaps preventing L9 from folding back into the pore lumen (FIG. 16). Furthermore, L9 and L10 were not altered in the protein prediction studies.

The mFhuA ΔC/Δ4L protein exhibited pore forming activity as evidenced by a discrete stepwise increase of current of ~200 pA at a transmembrane potential of 40 mV (FIG. 3A). On some occasions (less than ~5%), a pre-insertion activity of the mFhuA ΔC/Δ4L protein pore was observed (data not shown). Single-channels of the mFhuA ΔC/Δ4L protein pore showed irresolvable and infrequent downward current spikes with the amplitude of 15-70% of the unitary current (FIG. 3B and expanded trace). The mFhuA ΔC/Δ4L protein pore is characterized by a single-channel conductance of 4.8±1.3 nS (n=58) at the transmembrane potential of +40 mV (FIG. 3C and TABLE 3). An alternative way to determine the single-channel conductance of the mFhuA ΔC/Δ4L protein pore is to use the current versus voltage (I/V) curve (FIG. 3D). In this case, the slope of the I/V curve is exactly the single-channel conductance. It was discovered that the single-channel conductance of mFhuA ΔC/Δ4L pore is 5.7 nS in 1 M KCl, 10 mM potassium phosphate, pH 7.4, which falls within the standard error from the measurement using an applied transmembrane potential of +40 mV (TABLE 3). Furthermore, 67% of the channel conductance values fall within the standard error of the average single-channel conductance (FIG. 3C). In FIG. 3E, the voltage ramp recording is shown, which was obtained with two mFhuA ΔC/Δ4L protein pores inserted into the membrane. Insertions and closures of the mFhuA ΔC/Δ4L protein pores are observed during the voltage-ramp recording. Generally, the channel was not stable at an applied transmembrane potential greater than 50 mV (FIG. 3E).

EXAMPLE 6

Refolded FhuA ΔC/Δ4L Protein Forms a Channel that is Closely Similar to the Channel Formed by the Membrane-Extracted FhuA ΔC/Δ4L Protein The fundamental limitation of obtaining FhuA ΔC/Δ4L from the outer membrane by using detergent extraction protocol is that a significant amount of expressed protein ends up in inclusion bodies. Therefore, the refolded FhuA ΔC/Δ4L (rFhuA ΔC/Δ4L) protein pore was obtained from inclusion bodies using an improved and extensive on-column refolding protocol, which was followed by ion-exchange chromatography to separate folded from unfolded proteins.

Two assays were used to monitor the refolding of the FhuA ΔC/Δ4L protein, circular dichroism ("CD") spectroscopy and single-channel electrical recordings. The CD spectrum of the rFhuA ΔC/Δ4L protein showed a signature of high β-sheet containing proteins with a large positive peak located at 196 nm and a well defined minimum located at 217 nm (FIG. 4A). This spectrum is similar to that of membrane-extracted WT-FhuA. To interpret the secondary structures present in the rFhuA ΔC/Δ4L protein, web-assisted deconvolution of the CD spectrum was conducted using the CONTIN algorithm. The CD data analysis indicated the following protein structural content in rFhuAΔC/Δ4L: 40.8% β sheet, 3.7% α helix, 19.5% turns, and 37.2% disordered. Although the deconvolution of the CD spectrum of rFhuA ΔC/Δ4L indicates that the refolded protein retains the overall content of β structure, it cannot determine whether the protein forms a hollow β barrel.

The question of whether the rFhuA ΔC/Δ4L protein forms an open and stable channel that is closely similar to the mFhuA ΔC/Δ4L protein was also inspected. Indeed, the rFhuA ΔC/Δ4L protein readily inserted in the lipid bilayer, as indicated by a discrete stepwise increase of ~100 pA in the current at an applied transmembrane potential of +20 mV (FIG. 4B). Similar to the mFhuA ΔC/Δ4L protein, rFhuA ΔC/Δ4L exhibited irresolvable and rare current spikes (FIG. 4C and expanded trace). The single-channel conductance of the rFhuA ΔC/Δ4L protein was comparable with that of the mFhuA ΔC/Δ4L protein pore (4.9±0.7 nS, n=25) at an applied transmembrane potential of +40 mV (TABLE 3). In contrast to mFhuA ΔC/Δ4L, the rFhuA ΔC/Δ4L protein pore did not show a broad spectrum of single-channel conductance values (FIGS. 3C and 4D). Finally, the conductance of the rFhuA ΔC/Δ4L pore was measured using the I/V curve. The rFhuA ΔC/Δ4L protein pore showed an I/V curve that was closely similar to that measured with the mFhuA ΔC/Δ4L protein pore (FIG. 4E). The single-channel conductance was ~5.4 nS, which is in accord with the measurement performed at an applied transmembrane potential of +40 mV (TABLE 3). As in case of mFhuA ΔC/Δ4L, 68% of channels conductance values fall within the standard error of the average single-channel conductance (FIG. 4D).

EXAMPLE 7

Sensing of Polypeptides

To verify the capabilities of FhuA ΔC/Δ4L for sensing polypeptides, three structurally different polypeptides with almost the same charge density were chosen, including the α-helical Syn B2, the zinc-finger containing HIV-1 nucleocapsid protein (NCp7) and $pb_2(35)$-Ba (the small ribonuclease barnase with a leading domain that aids the interaction with the pore). See FIGS. 17A-19B, and TABLE 4. In TABLE 4: (i) the charge is estimated at pH 7.4, except for $pb_2(35)$-Ba for which the charge was calculated for only the first 35 amino acids; (ii) the charge density was calculated as the number of positively charged amino acids divided by the total number of amino acids; (iii) all experiments were carried out in symmetrical conditions of 1 M KCl, 10 mM potassium phosphate, pH 7.4. A 50 μM, 10 μM and 0.2 μM of SynB 2, Ncp7 and $pb_2(35)$-Ba, respectively, were added to the trans chamber; and (iv) values for $K_{off}(S^{-1}) \times 10^{-3}$ represent means±SDs calculated from three separate single-channel experiments.

TABLE 4

Analyte properties and their interaction kinetics with FhuA Δ4L pore.

| Analyte/number of amino acids | Charge | Charge density | $K_{on}(M^{-1}S^{-1}) \times 10^{-5}$ | $K_{off}(S^{-1}) \times 10^{-3}$ |
|---|---|---|---|---|
| Syn B2/23 | +5 | 0.2 | 22 ± 6 | 8.3 ± 2.2 |
| NCp7/55 | +8 | 0.17 | 20 ± 2 | 9 ± 0.8 |
| $pb_2(35)$-Ba/35 | +7 | 0.2 | 1.8 ± 0.3 | 11 ± 2 |

Figure 17A:
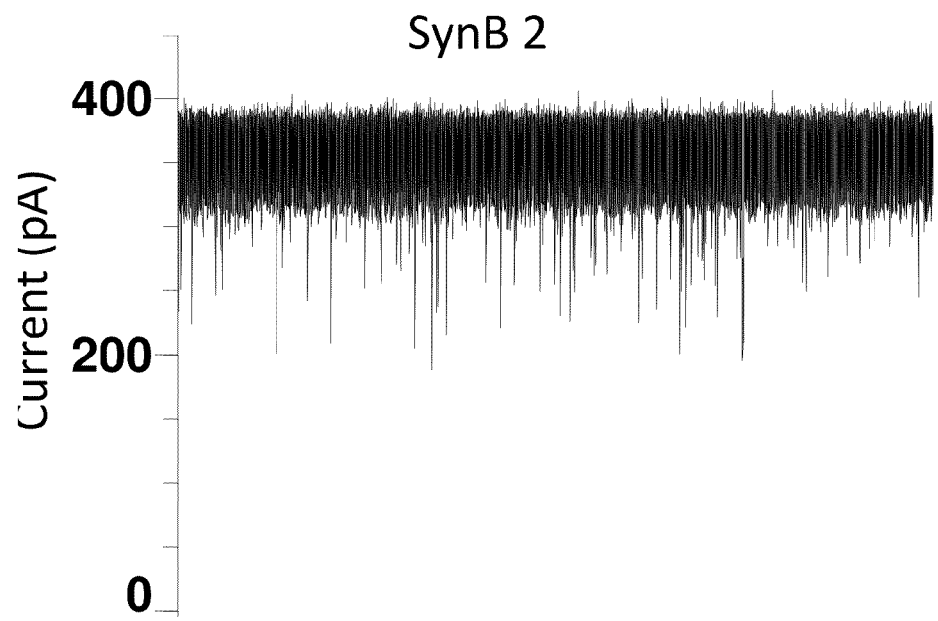
FIG. 17 is: (A) a graph of representative single-channel electrical recordings of the FhuA ΔC/Δ4L pore with SynB 2 (5 μM), which were performed at room temperature in 1 M KCl, 10 mM potassium phosphate, pH 7.4 with a transmembrane potential of +80 mV; and (b) semilogarithmic plots of all points histogram of single channels in the presence of SynB 2 (5 μM)
Figure 17B:
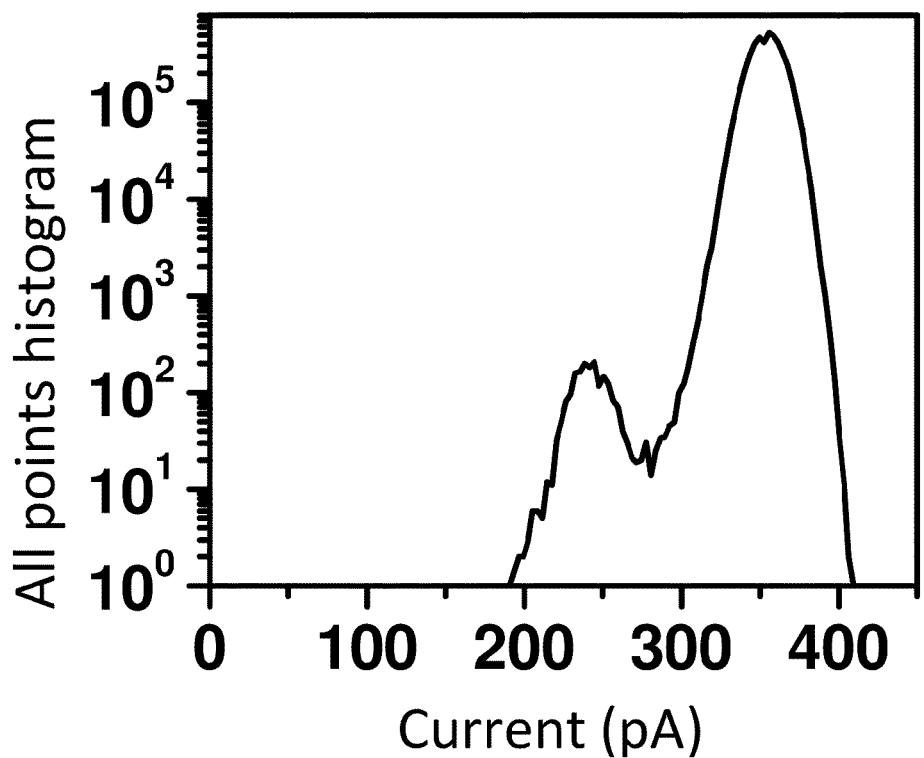
Figure 18A:
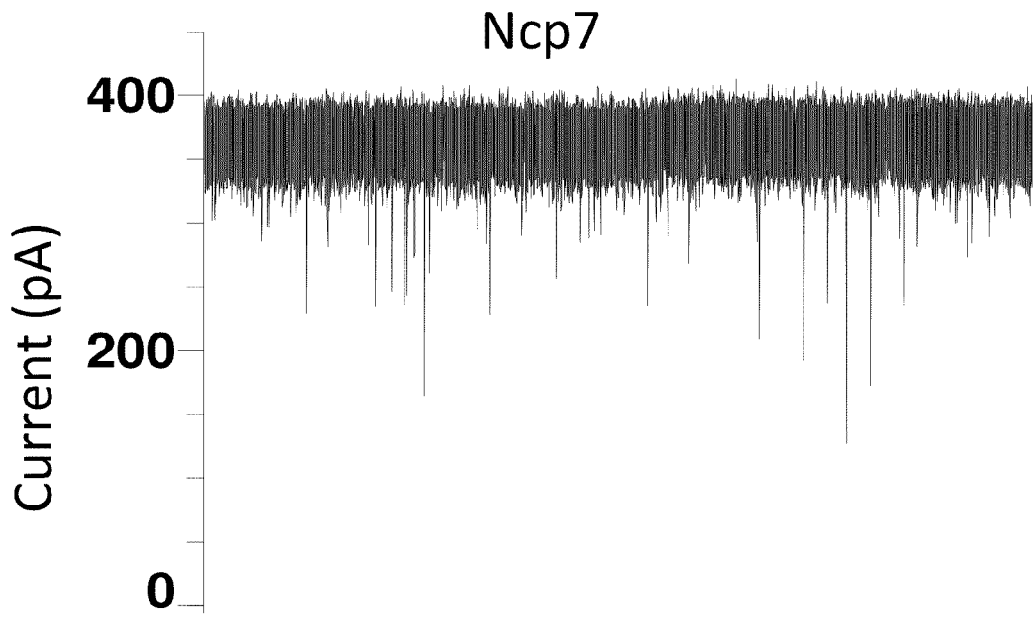
FIG. 18 is: (A) a graph of representative single-channel electrical recordings of the FhuA ΔC/Δ4L pore with Ncp7 (0.2 μM), which were performed at room temperature in 1 M KCl, 10 mM potassium phosphate, pH 7.4 with a transmembrane potential of +80 mV; and (B) semilogarithmic plots of all points histogram of single channels in the presence of Ncp7 (0.2 μM)
Figure 18B:
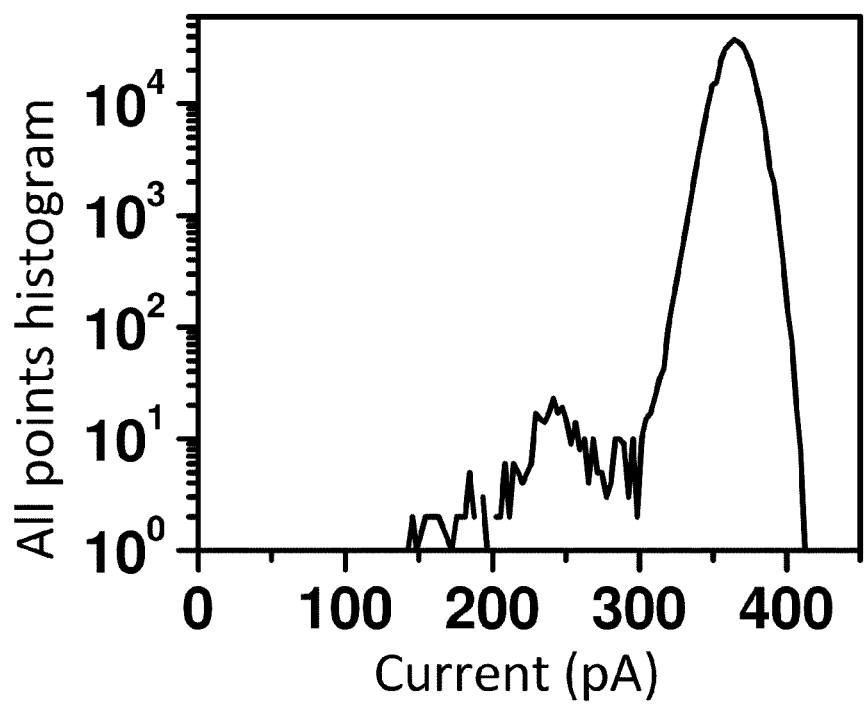
Figure 19A:
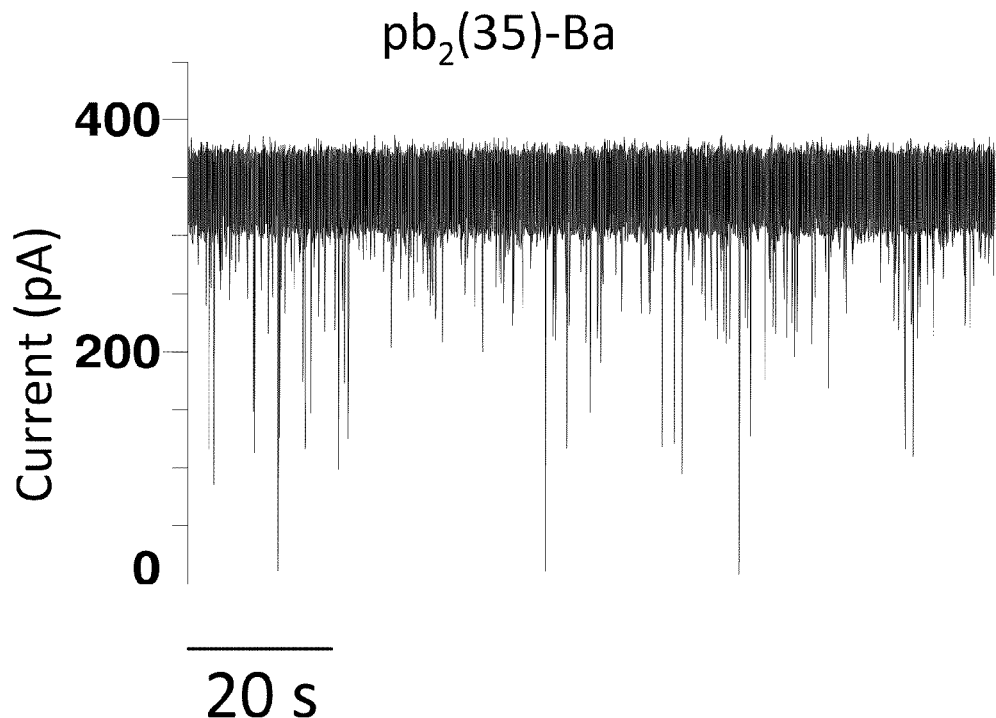
FIG. 19 is: (A) a graph of representative single-channel electrical recordings of the FhuA ΔC/Δ4L pore with $pb_2$ (35)-Ba (0.2 μM), which were performed at room temperature in 1 M KCl, 10 mM potassium phosphate, pH 7.4 with a transmembrane potential of +80 mV; and (B) semilogarithmic plots of all points histogram of single channels in the presence of $pb_2$ (35)-Ba (0.2 μM)
Figure 19B:
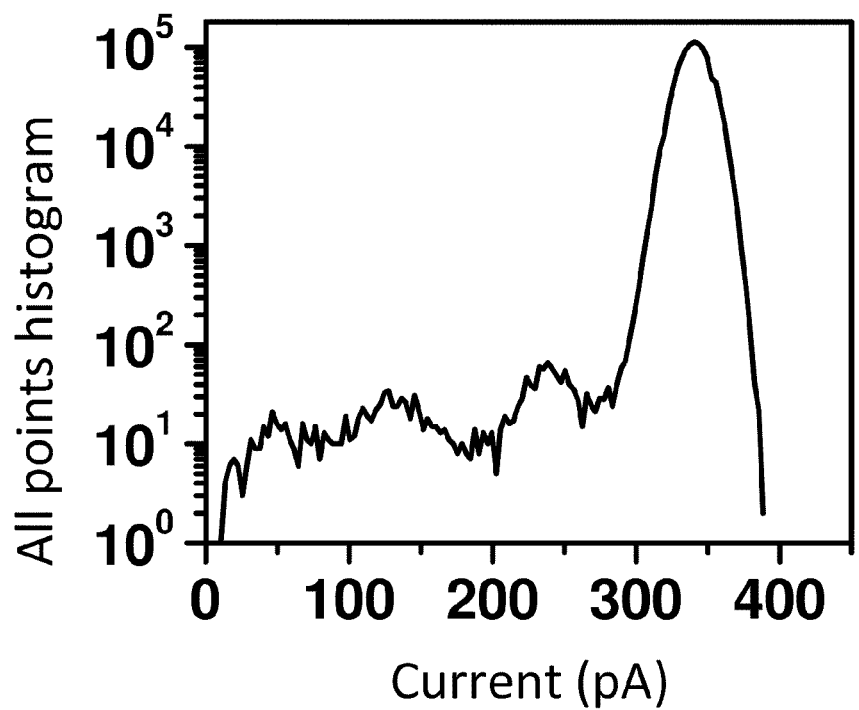
Figure 20A:
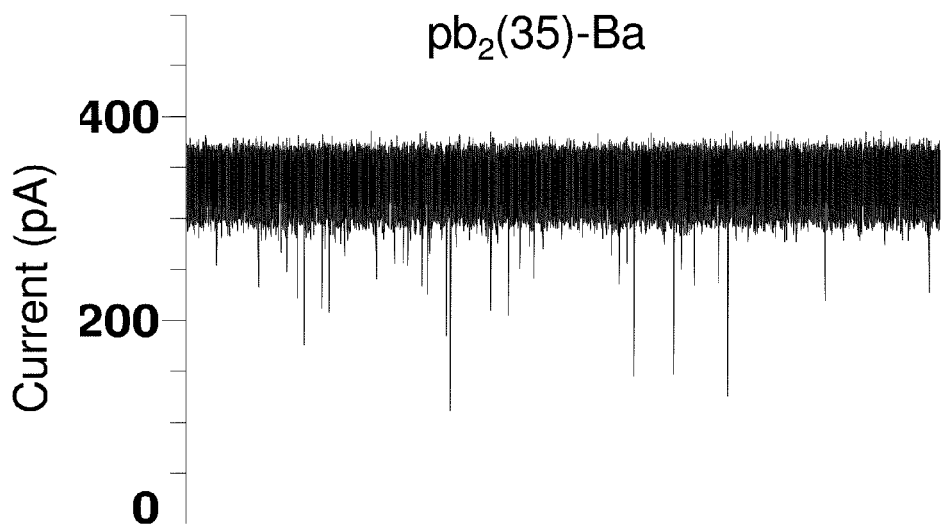
FIG. 20 is: (A) a graph of the single-channel electrical recordings with the engineered FhuA ΔC/Δ4L pore and $pb_2$ (35)-Ba (0.2 μM) added to the trans chamber, with the single-channel recordings were performed at room temperature in 1 M KCl, 10 mM potassium phosphate, and pH 7.4 with an applied transmembrane potential of +80 mV; and (B) a graph of the single-channel electrical recordings with the engineered FhuA ΔC/Δ4L pore and $pb_2$(65)-Ba (0.2 μM) added to the trans chamber, with the single-channel recordings were performed at room temperature in 1 M KCl, 10 mM potassium phosphate, and pH 7.4 with an applied transmembrane potential of +80 mV.
Figure 20B:
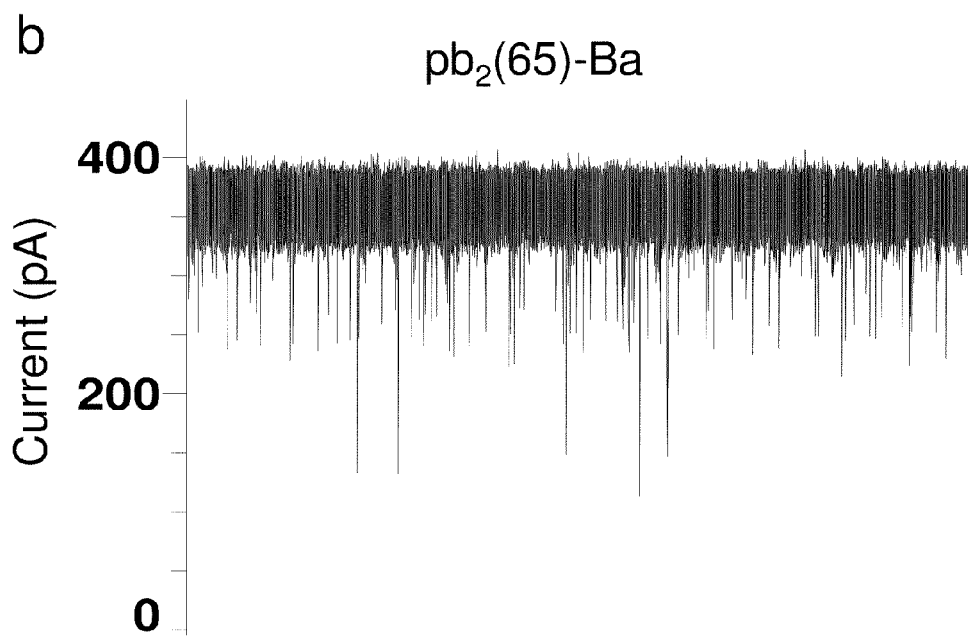
Figure 21:
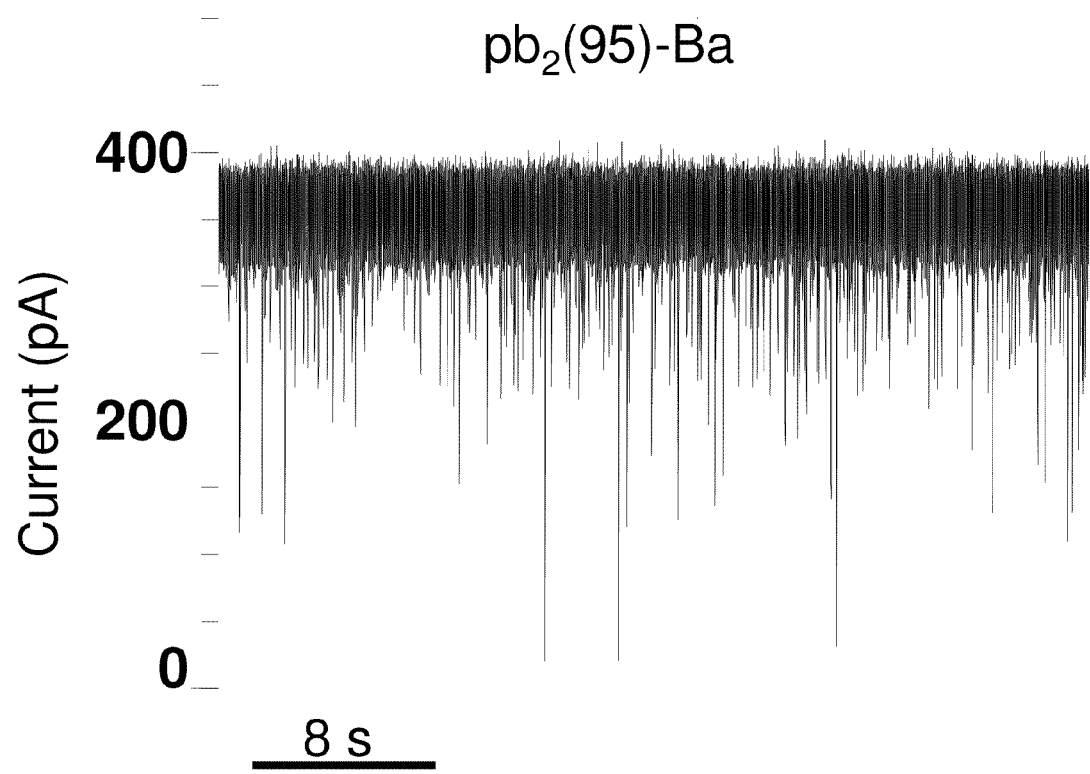
FIG. 21 is a graph of the single-channel electrical recordings with the engineered FhuA ΔC/Δ4L pore and pb$_2$(95)-Ba (0.2 μM) added to the trans chamber, with the single-channel recordings were performed at room temperature in 1 M KCl, 10 mM potassium phosphate, and pH 7.4 with an applied transmembrane potential of +80 mV.

When Syn B2 was added to the trans side of the chamber in the single-channel recording, it induced numerous events which reduced the current by 22%-47% with an applied potential of +80 mV, as shown in FIGS. 17A and 17B. As a control, the single-channel trace is quiet without the addition of polypeptides. When an α-HL pore (1.5 nm) was used with the same polypeptide under identical conditions, the current was reduced to 70%-95%, this indicates that FhuA ΔC/Δ4L is a pore with a wider lumen, that allows more ions to pass through the pore along with the polypeptide in comparison to αHL pore. When the NCp7 protein was added to the trans chamber, the current was reduced moderately by 22%-64%, FIGS. 18A and 18B, suggesting that the NCp7 occludes more ions from passing through the pore by its two zinc fingers. A dramatic current reduction was observed, 22%-95%, when the $pb_2(35)$-Ba protein was used, as shown in FIGS. 19A and 19B. This was interpreted to mean that this large reduction of current is caused by the Barnase domain of the $pb_2(35)$-Ba being pulled by the leading domain toward the pore with the applied potential. It is not expected that the unstructured leading domain of $pb_2(35)$-Ba causes the current reduction, as it is not wide enough to totally block the pore. Interestingly, the same Ba domain shows different interactions when fused to various leading domains (interaction domains), as shown in FIGS. 20 and 21.

To further analyze the interaction of the FhuA Δ/CΔ4L pore with Syn B2, NCp7 and $pb_2(35)$-Ba, two parameters were derived from the partition time and the frequency of events: the rate of disassociation ($k_{off}$) and the rate of association ($k_{on}$), respectively. It was observed that the $k_{off}$ increased and $k_{on}$ decreased, indicating that the kinetics of the FhuA Δ/CΔ4L interaction with different analytes is affected by the overall structure and composition of the analytes. More importantly, the engineered protein pore has the capability to sense and differentiate between these analytes. This capability opens unprecedented opportunity to explore pores for studying different protein domains at single-molecule level.

Figure 22:
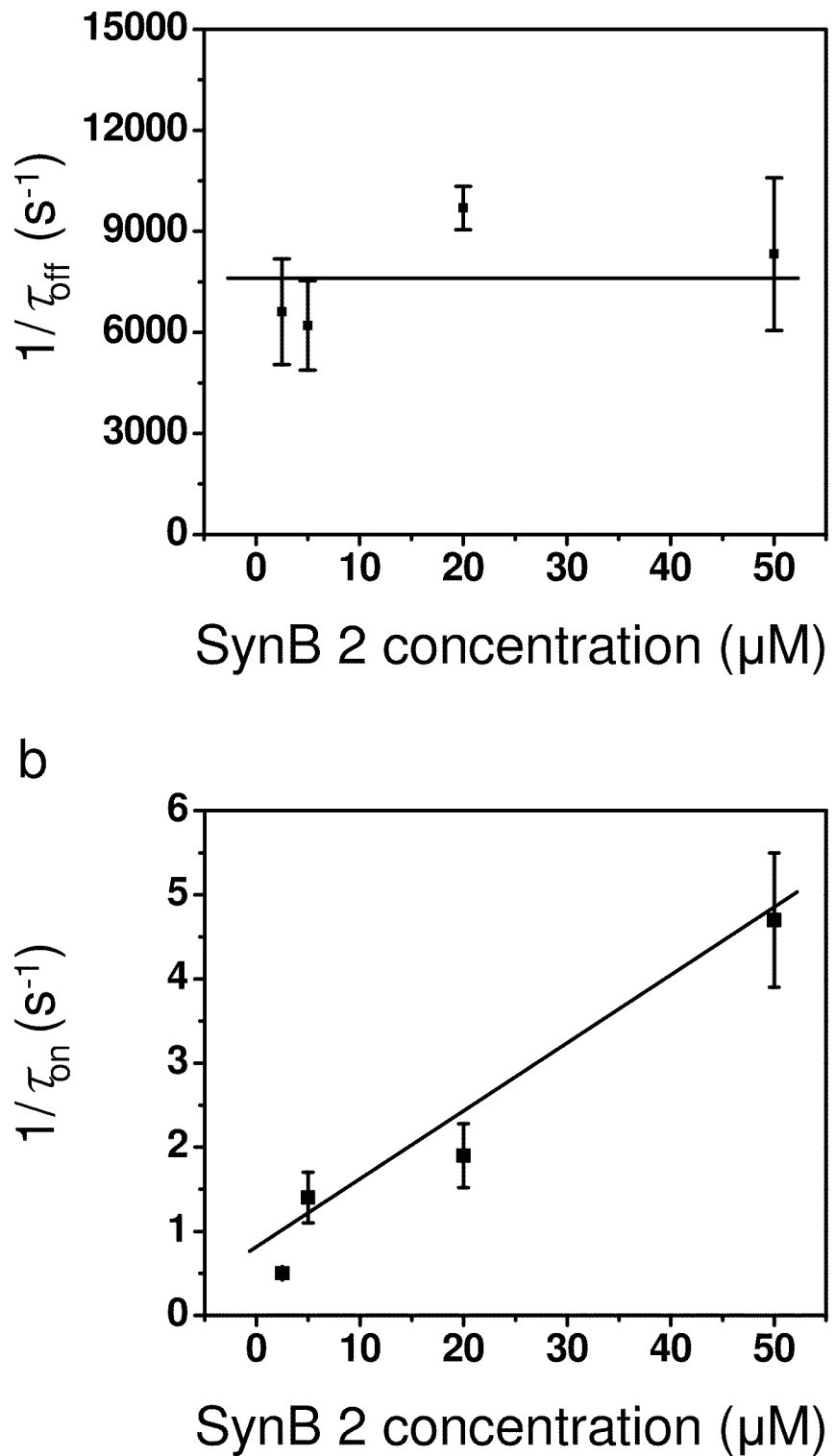
FIG. 22 is: (A) a graph of the dose-response dependence of the 1/$\tau_{off}$ values, where all measurements were carried out at room temperature in 1 M KCl, 10 mM potassium phosphate, and pH 7.4, and the transmembrane potential was +80 mV; and (B) a graph of the dose-response dependence of the 1/$\tau_{on}$ values, where all measurements were carried out at room temperature in 1 M KCl, 10 mM potassium phosphate, and pH 7.4, and the transmembrane potential was +80 mV.
Figure 23:
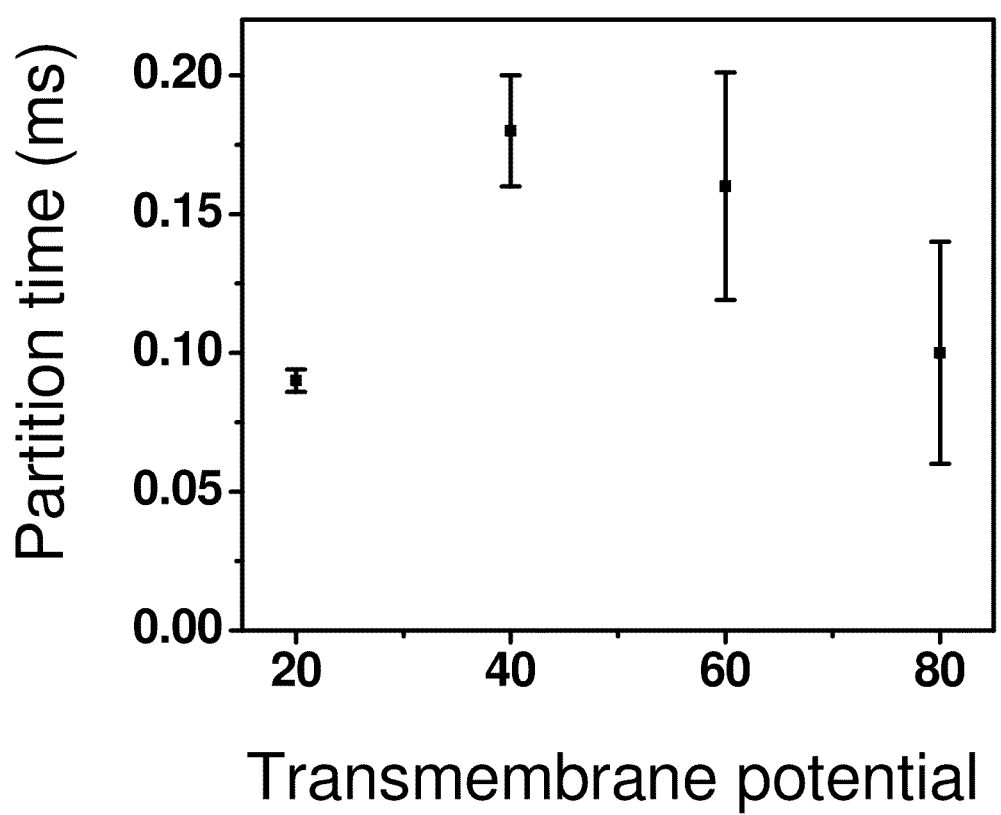
FIG. 23 is a graph of the voltage-dependence of the rate constants of dissociation $\tau_{off}$, where all measurements were carried out at room temperature in 1 M KCl, 10 mM potassium phosphate, and pH 7.4, and the transmembrane potential was +80 mV.

It was a further aim to determine whether the interactions between FhuA Δ/CΔ4L and the various analytes are bimolecular, as this kind of interaction is needed for future biosensor development. Syn B2 was used to demonstrate the nature of the interaction between an analyte and the FhuA Δ/CΔ4L pore. At various concentrations of Syn B2, it was found that the partition time ($\tau_{off}$) is independent of the polypeptide concentrations, see FIG. 22A, whereas the reciprocal of the mean inter-event interval ($\tau_{on}$) is linearly dependent on the polypeptide concentration, as shown in FIG. 22B. These results suggest that the interaction between Syn B2 and FhuA Δ/CΔ4L is bimolecular. Further, the partition time of Syn B2 is biphasic in nature at different applied potentials that indicates major partitioning of the polypeptides into the FhuA Δ/CΔ4L lumen, as shown in FIG. 23.

EXAMPLE 8

Differential Sensing of Proteins Analytes with Varying Interaction Domains

It was a further aim to explore the sensing capabilities of FhuA Δ/CΔ4L by examining its interaction with analytes of the same globular domain attached to different interaction domains. To achieve this, the first 35, 65, and 95 amino acids of the positively charged N-terminal region of pre-cytochrome $b_2$ ($pb_2$) was fused to the folded ribonuclease barnase (Ba) protein, resulting in protein constructs $pb_2(35)$-Ba, $pb_2(65)$-Ba, and $pb_2(95)$-Ba, respectively. See FIGS. 20 and 21, and TABLE 4. The following applies to TABLE 4: (i) the charge is estimated at pH 7.4, and the charge was calculated for only the first 35, 65, and 95 amino acids from $pb_2(35)$-Ba, $pb_2(65)$-Ba and $pb_2(95)$-Ba, respectfully; (ii) the charge density was calculated as the number of positively charged amino acids divided by the total number of amino acids; (iii) all experiments were carried out in symmetrical conditions of 1 M KCl, 10 mM potassium phosphate, pH 7.4. 0.2 μM of each protein were added to the trans chamber; and (iv) the values represent means±SDs calculated from three separate single-channel experiments.

TABLE 4

Proteins properties and their interaction kinetics with FhuA ΔC/Δ4L pore.

| Analyte | Charge | Charge density | $k_{on}$ (M$^{-1}$S$^{-1}$)× 10$^{-5}$ | $k_{off}$ (S$^{-1}$)× 10$^{-3}$ |
|---|---|---|---|---|
| pb$_2$(35)-Ba | +7 | 0.2 | 1.1 ± 0.3 | 11 ± 2 |
| pb$_2$(65)-Ba | +13 | 0.2 | 2.0 ± 0.3 | 9 ± 0.4 |
| pb$_2$(95)-Ba | +16 | 0.17 | 2.8 ± 0.2 | 3 ± 0.1 |

The crystal structure of the FhuA protein shows numerous pools of negatively charged residues within the pore lumen. In agreement with this observation, it was found that the FhuA ΔC/Δ4L protein nanopore exhibits the permeability ratio $P_K/P_{Cl}$ of 5.5±1.7 in asymmetric condition of 20 mM KCl/200 mM KCl. A cation-selective open FhuA nanopore might serve as a receptor for positively charged polypeptides. Therefore, it was desirable to investigate the interactions of the engineered FhuA ΔC/Δ4L protein nanopore with folded protein domains decorated by positively charged polypeptides. The target protein was the small, globular 110-residue RNAase barnase fused to the unstructured N-terminal part of the pb$_2$ pre-cytochrome. Three pb$_2$-Ba proteins of varying length and similar electric charge density of the pb$_2$ presequence were used (TABLE 4).

First, single-channel recordings with the FhuA ΔC/Δ4L protein nanopore in the presence of 200 nM pb$_2$-Ba added to the trans side of the bilayer were executed. At a transmembrane potential of +80 mV and in 1 M KCl, 10 mM potassium phosphate, pH 7.4, all pb$_2$-Ba produced short-lived current blockades with an average dwell time of 0.20±0.08 ms (n=3), but each featured distinct association rate constants (TABLE 4). Different association rate constants derived with pb$_2$-Ba proteins of varying presequence length indicate that their interaction with the protein nanopore is strongly dependent on the leading polypeptide arm (TABLE 4, FIG. 24). The current blockades were interpreted to result from the direct interaction between the positively charged pb$_2$ arm and the negatively charged interior of the nanopore. A large folded protein domain, such as bovine serum albumin ("BSA"), did not produce single-channel current blockades when added to the trans side of the chamber. It was observed that increasing the applied transmembrane potential increased the closing probability of the nanopore, suggesting that the pb$_2$-Ba proteins did not traverse the nanopore.

Figure 24:
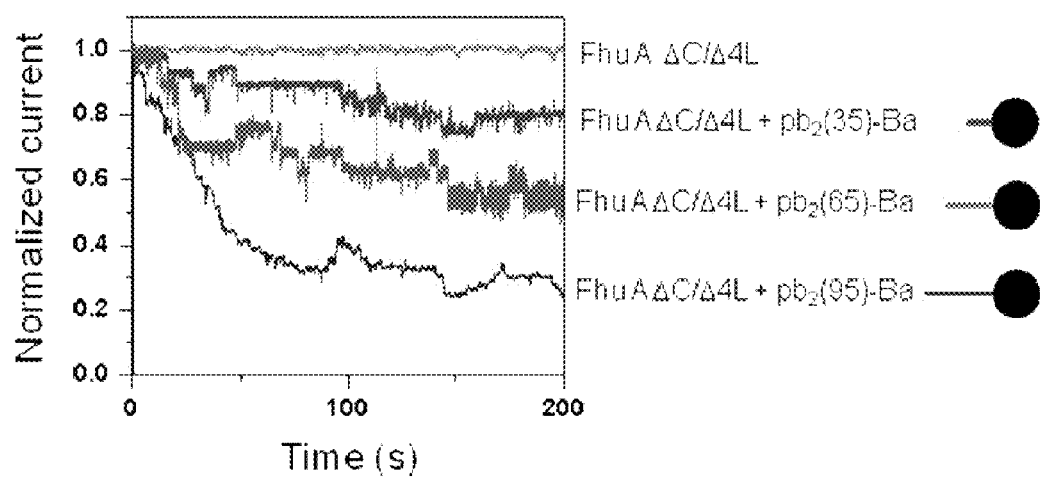
FIG. 24 is a graph of macroscopic currents normalized to the value that corresponded to the initial time of each electrical trace, where the chamber solution contained 20 mM KCl, 10 mM potassium phosphate, pH 7.4, and 100 nM pb$_2$-Ba was added to the trans side of the chamber.

Second, to amplify the strength of the electrostatic interactions between the FhuA ΔC/Δ4L nanopore and the pb$_2$-Ba proteins, multi-channel current measurements in 20 mM KCl were employed. The macroscopic current trace recorded with FhuA ΔC/Δ4L showed an open-state current (FIG. 24). A slow closure rate (<3×10$^{-3}$ s$^{-1}$) of the macroscopic current was noticed with the FhuA ΔC/Δ4L protein nanopore when 100 nM pb$_2$(35)-Ba was added to the trans side of the chamber. In contrast, a rapid decay of the macroscopic current was recorded with pb$_2$(95)-Ba with a rate constant of (28±9)×10$^{-3}$ s$^{-1}$ (n=4). The residual currents found with pb$_2$(35)-Ba, pb$_2$(65)-Ba and pb$_2$(95)-Ba were 0.72±0.18%, 0.55±0.17%, and 0.25±0.12%, respectively (FIG. 24, TABLE 4). This result is in accord with the single-channel recording data that established an increasing rate constant of association with an increase in the length of the pb$_2$ presequence. Distinct interactions of FhuA ΔC/Δ4L with pb$_2$-Ba proteins of varying pb$_2$ length indicate that the pb$_2$ arm partitions into the pore lumen.

To confirm that these events are true partitioning of the interaction domain of the analytes into the FhuA Δ4L lumen as opposed to the "bumping" of the analytes with the opening of the pore, higher voltages were applied. If the observed events are bumping events, then the partition time should not be effected; however, if they represent true partitioning then the partition time should increase with higher voltages, as the pulling force on the Ba domain increases. Indeed, it was observed that the partition time increases from is range at +80 mV to ~4 ms and +12 ms at +100 mV and +120 mV, respectively. These results indicate that the events produced by the protein analytes represent a true partitioning of the interaction domains into the FhuA Δ4L lumen.

Figure 25:
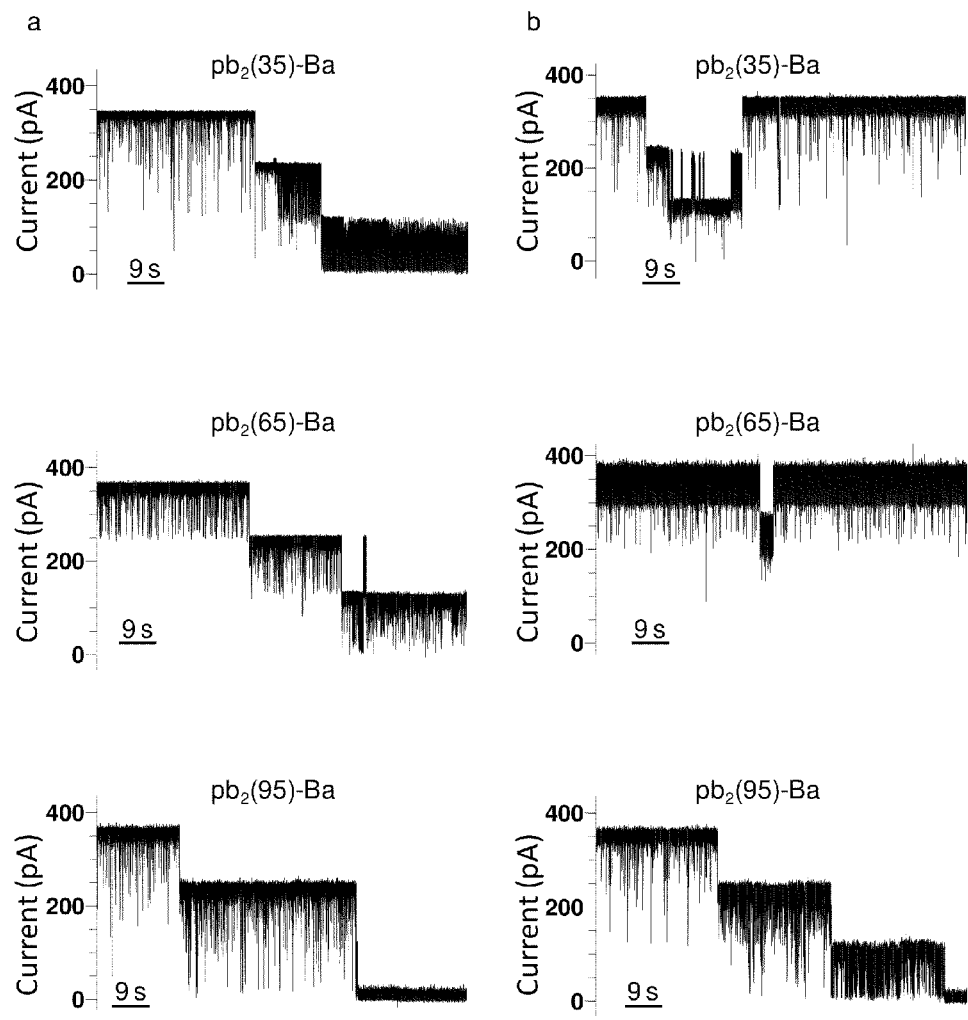
FIG. 25 shows graphs of single-channel recordings of pb$_2$(35)-Ba, pb$_2$(65)-Ba and pb$_2$(95)-Ba analytes, where the analytes either partition similarly into the pore (a), or show no pattern (b), where single-channel recordings were taken in 1M KCl, 10 mM potassium phosphate buffer, pH 7.4 and filtered at 2 kHz.

In previous work, each barnase construct required a different threshold of higher applied potential to show a similar interaction with the narrower αHL pore (1.5 nm); in fact, the αHL pore has to be engineered to lower the threshold of the applied potential to enhance the pore capability to sense these protein analytes. The partition of the interactions domains of these analytes resulted also in complete closures of the channels for longer time during the single-channel recordings. However, the nature of these closures of channels could not be correlated with the length of the interaction domains, as shown in FIG. 25.

The differential interaction of the FhuA Δ/CΔ4L pore with pb$_2$(35)-Ba, pb$_2$(65)-Ba and pb$_2$(95)-Ba can be seen in the rate of disassociation ($k_{off}$) and the rate of association ($k_{on}$) calculated from the interaction events prior to closure of the channels. The $k_{off}$ and $k_{on}$ increased with the length of the interaction domain of the Ba constructs, indicating that the kinetics of the FhuA Δ4L interaction with these analytes is dominated by the length of the interaction domains. Furthermore, this engineered pore has the potential to differentiate between modified proteins, and consequently cab be developed to detect structural modifications and changes in proteins.

EXAMPLE 9

Electrical Recordings on Planar Lipid Bilayers

Electrical recordings were carried out with planar bilayer lipid membranes ("BLMs"). The cis and trans chambers (1.5 mL each) of the apparatus were separated by a 25 um-thick Teflon septum (Goodfellow Corporation, Malvern, Pa.). An aperture in the septum of 80-120 um in diameter was pretreated with hexadecane (Sigma-Aldrich, St. Louis, Mo.) dissolved in highly purified pentane (Fisher HPLC grade, Fair lawn, NJ) at a concentration of 10% (vol/vol). A 1,2 diphytanoyl-sn-glycero-phosphatidylcholine (Avanti Polar Lipids, Alabaster, Ala.) bilayer was formed across the aperture. The FhuA wild-type and mutants pores were introduced by adding purified proteins to a final protein concentration of 100-180 ng/ml. Single-channel currents were recorded by using a patch clamp amplifier (Axopatch 200B, Axon Instruments, Foster City, Calif.) connected to Ag/AgCl electrodes through agarose bridges. The cis chamber was grounded so that a positive current (upward deflection) represents positive charge moving from the trans to cis side. An Optiplex Pentium PC (Dell Computers, Austin, Tex.) was equipped with a DigiData 1322A A/D converter (Axon) for data acquisition. The signal was low-pass filtered with an 8-pole Bessel filter (Model 900; Frequency Devices, Ottawa, Ill.) at a frequency of 10 kHz and sampled at 100 kHz, unless otherwise stated. For data acquisition and analysis, the pClamp9.2 software package (Axon) was used.

EXAMPLE 10

Plasmid Constructs

The pPR-IAB1 plasmids that contained wt fhua, and fhua Δ1-160, with an internal 6×His+ cloned into the coding region for the surfaced-exposed loop L5, were a gift. To construct fhua Δ322-355, inverse PCR was performed on the wt fhua-containing plasmid with the following two phosphorylated primers: p-322, 5'-GTG ATC GAA GCT GTA GCC GAC-3', (SEQ ID NO:1), and p-355, 5'-AAT GCT TAC AGC AAA CAG TGT-3' (SEQ ID NO:2). The resulting PCR products were gel-purified using the MinElute® gel purification kit (Qiagen, Germantown, Md.) and then self-ligated with T4 DNA ligase. To construct fhua Δ335-355, the same strategy was applied except that p-322 was exchanged with p-335, 5'-GCG CAG GTT CTG ACG CAC AGT-3' (SEQ ID NO:3). To construct fhua Δ1-160/Δ322-355 and fhua Δ1-160/Δ335-355, the above overall strategy was applied except that inverse PCR on the fhua Δ1-160-containing plasmid was performed. All constructs were verified by DNA sequencing.

The fhua gene lacking the loops 3, 4, 5, 11 and the first 160 amino acids, named fhua ΔC/Δ4 loops (called "fhua ΔC/Δ4l"), was constructed by de novo synthesis (Geneart®, Germany) in the pMK-RQ plasmid flanked by EcoRI and XhoI restriction sites for cloning purposes (see TABLE 5). In this construct, the deleted loops were replaced with NSEG(S) polypeptide linker. A serine residue was added, if it did not exist in the original loop. The pMK-RQ plasmid was digested with EcoRI and XhoI enzymes, and the released FhuA ΔC/Δ4L gene was gel purified using the Minielute gel purification kit (Qiagen®, USA) and cloned into pPR-IBA1 expression plasmid digested with EcoRI and XhoI enzymes. A C-terminal 6×His+ tag preceded by a thrombin protease cleavage site were added to FhuA ΔC/Δ4L by inverse PCR utilizing the following two primers: 5'-ACT ACC GCG TGG CAG CAG AAA ACG AAA GGT TGC GGT GGC AAC-3' (SEQ ID NO:4), and 5'-<u>CATCATCACCATCACCACTAA</u> AGC GCT GGG AGC CCC CCC AGT-3' (SEQ ID NO:5). The thrombin cleavage site and Histidine tag DNA sequences are bolded and underlined, respectively. The final plasmid was checked by DNA sequencing.

TABLE 5

The deleted loops in the FhuA ΔC/Δ4L protein.

| Loop | Deleted Amino Acids |
|---|---|
| L3 | 243-YYGWLPKEGTVEPLPNGKRLPTDFNEGAKNN-273 (SEQ ID NO: 6) |
| L4 | 318-CSDPANAYSKQCAALAPADKGH-339 (SEQ ID NO: 7) |
| L5 | 394-DDSVPLLNLYNPPDDLAVNTDFDFNAKDPAN-419 (SEQ ID NO: 8) |
| L11 | 692-NLFDREYVASCFNTYGCFWGAER-704 (SEQ ID NO: 9) |

TABLE 5 depicts the deleted loops in the FhuA Δ/CΔ4L protein, according to one embodiment of the present invention. In the table, the number in front of the loop is the number for the first amino acid of that loop. The number at the end of the loop is the number of the last amino acid of that loop. The letters represent the standard amino acid one-letter code.

EXAMPLE 11

Protein Expression and Purification

The pPR-IBA1 vector containing the fhua gene and its derived constructs were transformed into *E. coli* BL21 (DE3) omp9 (F⁻ hsdS$_B$ (r$_B^-$ m$_B^-$) gal ompT dcm (DE3) ΔlamB ompF::Tn5 ΔompA ΔompC ompN::'Ω. The transformed cells were grown in 2× TY media at 37° C., until an $A_{600}$~0.7-0.8, at which time the expression was induced with 1 mM isopropyl β-D-1-thiogalactopyranoside ("IPTG"). Expression was allowed to continue until the cell growth plateaued, as measured by $A_{600}$~1.4.

To purify the protein, the cells were harvested by centrifugation and then resuspended in resuspension buffer (50 mM Tris-Cl, pH 8.0, 100 mM NaCl, 10 mM MgCl$_2$, 10 ug/ml DNase I, protease inhibitors). The outer membranes were pre-extracted in 20 mM Tris, 1 mM EDTA, 0.1% octylpolyoxoethylene ("oPOE"), pH 8.0. The membrane-extracted proteins were obtained by incubating the outer membranes for 1 h at 37° C., while shaking at 200 rpm, in 20 mM Tris, 1 mM EDTA, 3% oPOE, pH 8.0. The insoluble materials were sedimented by centrifugation at 50,000×g for 45 min at 4° C.; the supernatant, enriched in extracted outer membrane proteins, was used for subsequent purification steps.

Prior to starting purification, the detergent concentration of the solubilized WT-FhuA was reduced from 3 to 1% to lessen the effects of detergent screening during chromatographic separation. Lower concentrations of oPOE were also tested; however, the concentrations were determined to be below the critical micelle concentration and thus did not allow for complete solubilization of the WT-FhuA protein. Following the decrease of the detergent concentration, the samples were loaded onto an UNO-Q strong anion exchange column (Bio-Rad) equilibrated with 25 mM Tris, 20 mM EDTA, 1% oPOE, pH 7.8, and eluted with 250-300 mM NaCl. The FhuA-containing fractions were then pooled and concentrated (Amicon 30K MWCO). In preparation for metal affinity chromatography, the buffer was exchanged, using a Bio-Select 250-5 SEC column (Bio-Rad), to 300 mM KCl, 50 mM KH2PO4, 5 mM imidazole, 1% oPOE, pH 8.0. FhuA-containing fractions were pooled and loaded onto an immobilized metal affinity column (Bio-Rad), equilibrated with 300 mM KCl, 50 mM KH2PO4, 5 mM imidazole, 1% oPOE, pH 8.0. The column was washed with 10 mM imidazole, and the bound proteins were eluted with 250 mM imidazole, analyzed by SDS-PAGE, and used for single-channel electrical recordings.

The harvested cells were resuspended in 50 ml of resuspension buffer (100 mM NaCl, 50 mM Tris-Cl, 10 mM MgCl2, pH 8.0, supplemented by 10 μg/ml DNase I and EDTA free-Complete protease inhibitors) (Roche Applied Science). The resuspended cells were lysed using a microfluidizer (Microfluidics). The homogenate was centrifuged for 20 min (2,000×g, 4° C.). The supernatant was then centrifuged for 1 h (180,000×g, 4° C.) to pellet the total membranes. The resulting pellet was then resuspended in resuspension buffer and centrifuged again for 1 h (180,000×g, 4° C.). The washed membrane-containing pellet was then suspended in n-laurylsarcosine-containing buffer (100 mM NaCl, 50 mM Tris-Cl, 2% n-laurylsarcosine (w/v), pH 8.0) and rotated overnight at 4° C. to selectively solubilize the inner membranes. The suspension was then ultracentrifuged for 1 h (180,000×g, 4° C.). The outer membrane containing pellet was resuspended in deionized double-distilled H2O and ultracentrifuged for 1 h (180,000×g, 4° C.). This step was repeated twice to ensure the elimination of residual detergent from the outer membrane-containing pellets. The washed pellets were then resuspended in outer membrane solubilization buffer (1% OG or 0.5% n-dodecyl β-D-maltoside (DDM), 100 mM NaCl, 50 mM Tris-Cl, 10 mM DTT, 0.1 mg/ml lysozyme, pH 8.0). The suspension was first rotated for 1 h at room temperature, followed by overnight rotation at 4° C., and then ultracentrifuged for 1 h (at 180,000×g, 4° C.) to separate the insoluble debris from solubilized outer membrane protein (FhuA ΔC/Δ4L). The OG- or DDM-solubilized FhuA ΔC/Δ4L was checked by SDS-PAGE and then stored at −80° C. 23 ml of solubilized FhuA ΔC/Δ4L was incubated with 2 ml of $Ni^{2+}$-nitrilotriacetic acid resin (equilibrated in 500 mM NaCl, 20 mM Tris-HCl, 1% OG or 0.5% DDM, pH 8.0) for 12 h at 4° C. while rotating. The resin was then collected in a 30-ml column and washed with 5 column bed volumes of 500 mM NaCl, 20 mM Tris-HCl, 1% OG or 0.5% DDM, pH 8.0, followed by 5 column bed volumes of 500 mM NaCl, 20 mM Tris-HCl, 10 mM imidazole, 1% OG or 0.5% DMM, pH 8.0, and finally eluted in 5 bed volumes of 500 mM NaCl, 20 mM Tris-HCl, 250 mM imidazole, 1% OG or 0.5% DDM, pH8.0. The FhuA ΔC/Δ4L-enriched fractions were pooled and ultraconcentrated by 30K Mr cutoff ultraconcentrators (Sartorius Stedim Biotech, Goettingen, Germany) and checked by SDS-PAGE.

To purify the single- and double-deletion FhuA proteins, cells expressing FhuA proteins Δ322-355 and Δ335-355 were resuspended in PBS (0.9% NaCl, 1 mM potassium phosphate, pH 7.3). FhuA proteins Δ1-160, Δ1-160/Δ322-355, and Δ1-160/Δ335-355 were resuspended in 20 mM NaH2PO4, pH 7.4. The cells were disrupted using either a Sonic Dismembrator model 500 (ThermoFisher, Waltham, Mass.) or a microfluidizer (Microfluidics, Newton, Mass.), after which the lysates were centrifuged at 8,500×g for 20 min at 4° C. The supernatant was then centrifuged at 180,000×g for 1 h at 4° C. The pelleted total membranes were then resuspended in Triton/urea buffer (50 mM Tris-HCl, 6 M urea, 2% Triton X-100, pH 8.0) or 20 mM NaH2PO4, 2% n-laurylsarcosine, pH 7.4, to solubilize the inner cell membranes. This was followed by rolling incubation at room temperature for 2 h and then centrifugation at 180,000×g for 1 h at 4° C. The outer membrane pellet was then resuspended in n-octyl β-D-glucopyranoside ("OG")/EDTA buffer (50 mM Tris-HCl, 1 mM EDTA, 33 mM OG, pH 8.0) or 20 mM NaH2PO4, 33 mM OG, pH 7.4, and rotated overnight. The suspension was then centrifuged at 180,000×g for 1 h at 4° C. The solubilized FhuA proteins Δ322-355, Δ335-355, Δ1-160/Δ322-355, and Δ1-160/Δ335-355 were then purified by ion exchange chromatography as in WT-FhuA except with OG-containing buffers, followed by size exclusion chromatography. Immobilized metal affinity column purification was performed with the above proteins but did not get the proteins bound to the column, presumably due to the 6×His⁺ tag not being accessible. For FhuA Δ1-160, the protein was purified utilizing the 6×His⁺ tag. The FhuA Δ1-160-containing supernatant was loaded onto a $Ni^{2+}$-nitrilotriacetic acid column (Qiagen), equilibrated in NPI-10 (300 mM NaCl, 50 mM NaH2PO4, 33 mM OG, 10 mM imidazole, pH 8.0). After washing the column with 6 column volumes with NPI-10 buffer, followed by a 6-column volumes wash with NPI-20 (300 mM NaCl, 50 mM NaH2PO4, 33 mM OG, 20 mM imidazole, pH 8.0), the FhuA proteins were eluted in NPI-150 (50 mM NaH2PO4, 300 mM NaCl, 33 mM OG, 150 mM imidazole, pH 8.0). Purity of the FhuA Δ1-160 protein was assessed by SDS-PAGE.

EXAMPLE 12

Refolding of FhuA Δ/CΔ4L from Inclusion Bodies

The harvested cells were then suspended in 50 ml of resuspension. The cells were then lysed using a microfluidizer (Microfluidics). The homogenate was then centrifuged for 10 min at 2,000×g, 4° C., to remove unbroken cells. The supernatant was then centrifuged at 30,000×g to pellet the inclusion bodies. The resulting pellet (inclusion bodies) was then resuspended in washing buffer (PBS, 1% Triton X-100, 1 mM EDTA, pH 7.4). The resuspended inclusion bodies were then centrifuged at 30,000×g for 30 min at 4° C. The washing step was repeated twice, and the resulting inclusion bodies were used for the subsequent refolding protocol. The inclusion bodies were resuspended in denaturing buffer (100 mM NaCl, 50 mM Tris-HCl, 8 M urea, pH 9.0) to a concentration of 15 mg/ml. Urea-assisted denaturation and solubilization was allowed to continue by rotating overnight at the ambient temperature. This was followed by clarification by centrifugation (30,000×g for 30 min at 4° C.). The clarified supernatant was loaded onto a Bio-Scale Mini Profinity™ immobilized metal affinity column cartridge (Bio-Rad) equilibrated in denaturing buffer. After washing the column five times, the concentration of denaturing buffer was linearly decreased, although the concentration of refolding buffer (50 mM Tris-HCl, 3 mM DTT, 1 mM EDTA, 79 mM urea, 1.23% (w/v) DDM, pH8.0) was linearly increased, followed by an incubation period of 24 h. The detergent concentration was then decreased with washing buffer (50 mM Tris-HCl, 1 mM EDTA, 0.25% (w/v) DDM, pH 8.0). Proteins were eluted with elution buffer (250 mM imidazole, 50 mM Tris-HCl, 1 mM EDTA, 1 M NaCl, 0.25% (w/v) DDM, pH 8.0). The eluted fractions were then checked by SDS-PAGE and stained with Invision His tag stain (Invitrogen), followed by colloidal blue staining using GelCode blue stain reagent (ThermoFisher). The FhuA ΔC/Δ4L-containing fractions were then pooled and concentrated, and the NaCl concentration was decreased using centrifugal filtration. The concentrated proteins were then loaded onto a MonoQcolumn (Bio-Rad) equilibrated with washing buffer (50 mM Tris-HCl, 1 mM EDTA, 0.25% (w/v) DDM, pH 8.0). A linear gradient of elution buffer (1 M NaCl, 50 mM Tris-HCl, 0.25% (w/v) DDM, pH 8.0) was applied, and the unfolded FhuA ΔC/Δ4L protein eluted first at ~75 mS/cm, although the folded FhuA ΔC/Δ4L protein eluted as a second peak at ~350 mS/cm.

EXAMPLE 13

Circular Dichroism Spectroscopy

All CD spectra were recorded on an Aviv 62DS circular dichroism spectropolarimeter (Aviv Instruments, Lakewood, N.J.) equipped with a temperature control unit. Quartz cuvettes with a 1 mm-path length were employed. Measurements were carried out at 20° C. over optical pathway of 1 mm, with a 1 nm step and a 10 s average time at protein concentration of 3.42 µM in 5 mM Tris, 100 mM NaCl, and 0.25% (w/v) DDM, pH 8.32. Deconvolution of the spectrum was accomplished using the CONTIN algorithm 1.

EXAMPLE 14

Prediction of Protein Structure

Energy minimization was performed using the INSIGHT II software package (MSI Scientific, San Diego, Calif.) with the modules View, Builder and Discover 3. The consistent valence force field (CVF) was used with a 10 Å cutoff, and 10000 minimization steps were run, 5000 iterations using the steepest descent gradient followed by 5000 iterations using conjugate gradients. For molecular dynamics (MD), a homology model for FhuA ΔC/Δ4L protein was constructed (Swiss Model). Then, it was used in a two-step molecular dynamics run. AMBER v11 was used in combination with the included force field and molecular simulations program. Minimization consisted of 100,000 steps with a 30 Å cutoff (50,000 steepest descent, which was followed by nearest neighbor algorithms). Molecular dynamics was then run under the following conditions: 30 Å cutoff, 250 ps run, 300° K, 2 fs time step, and solvated.

Standard MD simulations were also conducted to determine which loops may fold back into the pore lumen upon deletion of the N-terminal cork domain. For single and double deletion mutants, crystals structures obtained from the pdb ids 1BY5 and 2FCP were utilized. The cork domain (residues 1-160) was deleted and resulting structure was utilized to give an indication of which loops were to be further modified. Our standard MD simulations did not place our protein under an electric field. KCl was not included. Nonetheless, it provided us with key clues and assistance in the further rational design of the FhuA protein channel. Based on the MD simulations, four major loops exhibited high flexibility and a tendency to fold back into the cork-free pore lumen or to partially block access to it. These loops are L3, L4, L5 and L11.

Applications

The engineered proteins disclosed herein can be used for a wide variety of applications, including serving as wide-pore biosensors. For example, the engineered proteins can be used to detect modifications and/or alteration of DNA, including natural modifications such as methylation, or alteration such as damage in the DNA that result in DNA-adducts, among many other types of modifications and alterations. One of the many advantages of the engineered proteins disclosed above is that the nanopore is wide enough for, for example, dsDNA analysis.

Another use of the engineered proteins is to detect analytes and/or compounds on the surface of the nanopore. For example, the engineered proteins can be used to detect antigen/antibody interactions or receptor/ligand interactions. As just one example, prostate-specific antigen ("PSA") can be detected at the surface of the engineered proteins by modifying the protein nanopores. The engineered proteins are capable of interacting with and discriminating between modified protein substrates, resulting in numerous biosensor applications.

It should be noted that the applications provided above are provided only as an example of the many and varied applications, biosensor and otherwise, for which the engineered proteins may be used.

Further, although the present invention has been described in connection with particular embodiments, it should be understood that modifications, alterations, and additions can be made to the invention without departing from the scope of the invention as defined by the claims.

What is claimed is:

1. A polypeptide comprising an engineered ferric hydroxamate uptake component A ("FhuA") from *Escherichia coli*, wherein said engineered FhuA is missing the cork domain and four of the eleven loop domains found in a wild-type FhuA protein, and wherein said engineered FhuA is folded into a nanopore having a stable open-state current.

2. The polypeptide of claim 1, wherein said missing cork domain comprises the first 160 amino acid residues of the wild-type FhuA protein.

3. The polypeptide of claim 1, wherein said missing loop domains are loop 3, loop 4, loop 5, and loop 11.

4. The polypeptide of claim 1, wherein said missing loop domains are replaced by a short amino acid sequence having about five residues.

5. The polypeptide of claim 4, wherein said short amino acid sequence comprises Asparagine, Serine, Glutamate, Glycine, and Serine ("NSEGS") SEQ. ID NO: 10.

6. The polypeptide of claim 1, wherein said stable open-state current comprises the ability to maintain a steady open-state current for at least 200 seconds.

7. The polypeptide of claim 1, wherein said nanopore has a conductance of about 4.9 nS in 1 M KCL.

* * * * *